(12) United States Patent
Davidson et al.

(10) Patent No.: US 8,318,489 B2
(45) Date of Patent: Nov. 27, 2012

(54) PROSTACYCLIN DIRECTED DIFFERENTIATION OF CARDIOMYOCYTES FROM HUMAN EMBRYONIC STEM CELLS

(76) Inventors: Bruce Paul Davidson, Singapore (SG); Ralph Eberhard Graichen, Singapore (SG); Robert Zweigerdt, Singapore (SG); Xiuqin Xu, Singapore (SG); Christine Lindsay Mummery, DJ Bilthoven (NL); William Sun, Singapore (SG)

( * ) Notice: Subject to any disclaimer, the term of this patent is extended or adjusted under 35 U.S.C. 154(b) by 1027 days.

(21) Appl. No.: 12/158,521

(22) PCT Filed: Dec. 22, 2006

(86) PCT No.: PCT/AU2006/001969
§ 371 (c)(1),
(2), (4) Date: Nov. 7, 2008

(87) PCT Pub. No.: WO2007/070964
PCT Pub. Date: Jun. 28, 2007

(65) Prior Publication Data
US 2009/0202498 A1    Aug. 13, 2009

Related U.S. Application Data

(60) Provisional application No. 60/753,434, filed on Dec. 22, 2005.

(51) Int. Cl.
*C12N 5/02* (2006.01)
(52) U.S. Cl. ........................ 435/377; 435/384; 435/387
(58) Field of Classification Search .................. None
See application file for complete search history.

(56) References Cited

FOREIGN PATENT DOCUMENTS

| GB | 2 437 027 A | 10/2007 |
| GB | 2 444 686 A | 6/2008 |
| WO | WO 2004/065589 * | 8/2004 |
| WO | 2005/065354 A2 | 7/2005 |
| WO | WO 2005/117874 A1 | 12/2005 |
| WO | 2007/070964 A1 | 6/2007 |

OTHER PUBLICATIONS

Mummery et al. Differentiation of human embryonic stem cells to cardiomyocytes: role of coculture with visceral endoderm-like cells. Circulation, 2002, vol. 107, pp. 2733-2740.*
Pekkanen-Mattila et al. "Differentiation, Characterization and Applications of Human Embryonic Stem Cell—Derived Cardiomyocytes" Chapter 26, in Embryonic Stem Cells: The Hormonal Regulation of Pluripotency and Embryogenesis, Craig Atwood, ed., InTech, Croatia, 2011, pp. 505-522.*
Fukuhara et al. Direct cell-cell interaction of cardiomyocytes is key for bone marrow stromal cells to go into cardiac lineage in vitro. J. Thoracic Cardiovasc. Surgery, 2003, vol. 124, pp. 1470-1470.*
Liao et al. p38 Mitogen-Activated Protein Kinase Mediates a Negative Inotropic Effect in Cardiac Myocytes. Circulation Res., 2001, vol. 90, pp. 190-196.*
Sigma-Aldrich Catalog, 2011, Iscove Modified Dulbecco's Medium (IMDM.).*
Official Action dated Mar. 2, 2010 from corresponding UK Patent Application No. GB0812222.8.
Official Action dated Nov. 5, 2010 from corresponding UK Patent Application No. GB0812222.8.
Aouadi, M. et al., "p38 Mitogen-Activated Protein Kinase Activity Commits Embryonic Stem Cells to Either Neurogenesis or Cardiomyogenesis", *Stem Cells*, 24: 1399-1406 (2006).
Binétruy, B. et al., "Concise Review: Regulation of Embryonic Stem Cell Lineage Commitment by Mitogen-Activated Protein Kinases", *Stem Cells*, 25: 1090-1095 (2007).
Engel, F. B. et al., "p38 MAP kinase inhibition enables proliferation of adult mammalian cardiomyocytes", *Genes Dev*, 19(10): 11757-1187 (2005).
Qi, X. et al., "BMP4 supports self-renewal of embryonic stem cells by inhibiting mitogen-activated protein kinase pathways", *PNAS*, 101(16): 6027-6032 (2004).
Passier, R. et al., "Increases Cardiomyocyte Differentiation from Human Embryonic Stem Cells in Serum-Free Cultures", *Stem Cells* 23:772-780 (2005).
Sachinidis, A. et al., "Identification of Plateled-derived Growth Factor-BB as Cardiogenesis-Inducing Factor in Mouse Embryonic Stem Cells Under Serum-Free Conditions" *Cellular Physiology and Biochemistry* 13:423-429 (2003).
Suzuki, T. et al., "Serum-Free, Chemically Defined Medium to Evaluate the Direct Effects of Growth Factors and Inhibitors on Proliferation and Function of Neonatal Rat Cardiac Muscle Cells in Culture" *In Vitro Cellular & Developmental Biology* 25(7):601-606 (1989).
Nag, A.C. et al., "Factors Controlling Embryonic Heart Cell Proliferation in Serum-Free Synthetic Media" *In Vitro Cellular & Developmental Biology* 21(10):553-562 (1985).
Wei, H. et al., "Embryonic Stem Cells and Cardiomyocyte Differentiation: Phenotypic and Molecular Analyses" *Journal of Cellular and Molecular Medicine* 9(4): 804-817 (2005).

* cited by examiner

*Primary Examiner* — Deborah Crouch
(74) *Attorney, Agent, or Firm* — E. Stewart Mittler

(57) ABSTRACT

The present invention relates to the induction of differentiation in stem cells to cardiomyocytes and factors such as prostaglandin alone or in combination with other factors including essential minerals selected from the group including transferrin and selenium, small molecules selected from the group including a p38 MAPK inhibitor such as SB203580 and protein growth factors of the FGF, IGF and BMP families such as but not limited to IGF1, FGF2, BMP2, BMP4 and BMP6. and insulin that influence the process of differentiation to cardiomyocytes. Media that is appropriate for the induction of differentiation of cardiomyocytes from stem cells is also provided wherein the media contains these factors. The use of cardiomyocytes and cardiac progenitors produced by the directed differentiation in transplantation and screening for cardiac compounds is also provided.

14 Claims, 14 Drawing Sheets

A.

B.

C.

A.

B.

A.

B.

A.

B.

A.

B.

C.

A.

B.

C.

A.

B.

A.

B

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
attgctgaaa ccgagaatgg					20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
cgctccttga ggttgaaaag					20

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
ttactggcat tccagctcct					20

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
gggcacgacc tcatcttcta					20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
caatgtggcc gaggactttg					20

<210> SEQ ID NO 6
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 6
cattctcctt agagagaagt gg					22

PROSTACYCLIN DIRECTED DIFFERENTIATION OF CARDIOMYOCYTES FROM HUMAN EMBRYONIC STEM CELLS

CROSS-REFERENCE TO RELATED APPLICATIONS

This application claims the benefit of U.S. Provisional application No. 60/753,434 filed on Dec. 22, 2005.

The present invention relates to the induction of differentiation in stem cells, preferably human embryonic stem (hES) cells to cardiomyocytes and cardiac progenitors and factors that influence the induction of differentiation. Media for the induction of differentiation of cardiomyocytes from stem cells, preferably hES cells is also provided.

BACKGROUND

Cardiomyocytes are thought to be terminally differentiated. Although a small percentage of the cells may have proliferative capacity, it is not sufficient to replace injured or dead cardiomyocytes. Death of cardiomyocytes occurs, for example, when a coronary vessel is occluded by a thrombus and the surrounding cardiomyocytes cannot be supplied with necessary energy sources from other coronary vessels. Loss of functional cardiomyocytes may lead to chronic heart failure.

The proliferative capacity of the cardiomyocytes is not sufficient to regenerate the heart following myocardial injury. Conventional pharmacological therapy for patients with different stages of ischemic heart disease improves cardiac function, survival and quality of life. However, ischemic heart disease is still the most life-threatening disease in western society and alternative therapies will be necessary to improve the clinical outcome for patients with ischemic heart disease further. In recent years, the focus on cell replacement therapy has been intensified, stimulated by the increasing number of potential cell sources for transplantation, such as skeletal myoblasts, adult cardiac stem cells, bone marrow stem cells and embryonic stem cells.

A potential route for restoring "normal" heart function is replacement of injured or dead cardiomyocytes by new functional cardiomyocytes. Human embryonic stem (hES) cells are a potential source of cells for cardiomyocyte replacement. Either spontaneously, or upon induction, differentiation of hES cells into cardiomyocytes can be achieved.

Embryonic stem cells can differentiate to cardiomyocytes in culture, opening the possibility for controlled in vitro studies of developing human heart cells. However, it is difficult to control and induce the specific differentiation of ES cells solely towards cardiomyocytes (Brand, 2003).

Co-culturing END2 cells with hES cells can induce cardiomyocyte differentiation of the hES cells in serum-free culture conditions (Passier, et al, 2005). An END2 conditioned media (END2-CM) system has also been demonstrated to induce robust differentiation of cardiomyocytes in hES-derived embryoid bodies. Using feeder-free conditioned media allows for a more clean and controlled differentiation of cardiomyocytes than co-culturing. However, the END2-CM contains proteins and other molecules released from mouse END2 cells and as such hES cell-derived cardiomyocytes cultured from END2-CM would be considered a "xenoproduct" for clinical purposes. Therefore, identification of the "factor(s)" produced by the END2 cell line is of paramount importance to the development of a hES-derived therapeutic product.

Identifying the END2 inducing factors and other factors involved in the differentiation process has been challenging and illusive since the generation of the visceral-endoderm-like END2 cell line from a mouse P19 embryonic carcinoma cell line (Mummery, 1991). Earlier data has suggested that the END2 "factor" is secreted and it is a protein (van den et al, 1991). Regardless of its uncertainty on whether it is protein, it is important to identify the factor(s) if a therapeutically acceptable product is to be developed. Identifying cardiomyocyte inducing factors will provide opportunities to develop clinically compliant populations of hES cell-derived cardiomyocytes.

If differentiation conditions can be established with defined culturing conditions, and without the potential presence of animal pathogens, hES cell derived cardiomyocytes may be produced safely which are suitable for cardiomyocyte transplantation in patients with heart disease.

Accordingly, the invention seeks to identify factors that are involved in the process of cardiomyocyte differentiation and provide a defined culture system that is suitable for the induction of stem cells to cardiomyocytes and cardiac progenitors.

SUMMARY OF THE INVENTION

In a first aspect of the present invention there is provided a method of inducing cardiomyocyte differentiation of a human stem cell, the method comprising culturing the stem cell in the presence of a prostaglandin, analogue or functional equivalent thereof alone or in combination with other factors described herein such as essential minerals selected from the group including transferrin and selenium, small molecules selected from the group including a p38 MAPK inhibitor such as SB203580 and protein growth factors of the FGF, IGF and BMP families such as but not limited to IGF1, FGF2, BMP2, BMP4 and BMP6 a homologue or functional equivalent thereof.

Prostaglandin I2 has now been identified as an inducing factor alone or in combination with several growth factors or small molecules which may act as inducing or enhancing factors to directly differentiate human stem cells into cardiomyocyte induction.

In another aspect of the present invention, there is provided a culture media when used for the induction of cardiomyocyte differentiation in stem cells, said media comprising a prostaglandin, analogue or functional equivalent thereof alone or in combination with other factors described herein such as essential minerals selected from the group including transferrin and selenium, small molecules selected from the group including a p38 MAPK inhibitor such as SB203580 and protein growth factors of the FGF, IGF and BMP families such as but not limited to IGF1, FGF2, BMP2, BMP4 and BMP6 a homologue or functional equivalent thereof. Preferably, the prostaglandin, analogue or functional equivalent thereof is prostacyclin (PGI2), an analogue or functional equivalent thereof.

In another aspect of the present invention there is provided a method of inducing cardiomyocyte differentiation of a stem cell, the method comprising culturing the cells in the presence of a gene product expressed from a gene listed in Table 1.

In yet another aspect of the present invention there is provided a culture media when used for the induction of cardiomyocyte differentiation in stem cells, said media comprising a gene product expressed from a gene listed in Table 1.

In another aspect of the present invention there is provided a method of further enhancing induction of cardiomyocyte differentiation from a co-culture of a stem cell and an embryonic cell, said method comprising further inducing expression of a gene product expressed from a gene listed in Table 1.

In another aspect of the invention there is provided a method of further enhancing induction of cardiomyocyte differentiation said method comprising culturing the stem cell and conditioned media from a culture of an embryonic cell, in the presence of a gene product expressed from a gene listed in Table 1.

Ideally the gene product is expressed from a gene listed in Table 1. The gene product may be expressed from a gene selected from the group consisting of Bmp6, Fgf9, Bmp4, Scf, Bmp6, Igf2, Ptgis and Ptgs1. These genes will encode for gene products that affect and induce cardiomyocyte differentiation.

In yet another aspect there is provided a method of further enhancing induction of cardiomyocyte differentiation said method comprising culturing the stem cell and conditioned media from a culture of an embryonic cell, in the presence of a product selected from the group including Fgf9, Bmp6, Bmp4, Scf, Igf2 and Ptgis and Ptgs1.

In another aspect of the present invention there is provided a method of enabling cardiomyocyte differentiation in a stem cell culture said method comprising reducing an effect caused by insulin or an analogue thereof on the stem cell in culture.

It has now been found that media depleted in insulin is permissive for cardiomyocyte formation from stem cells. Without being limited by theory, the depletion of insulin and possibly other inhibitory factors allows or permits the stem cells to progress toward differentiation to a cardiomyocyte lineage.

In another aspect of the invention there is provided a method of enabling cardiomyocyte differentiation in a stem cell culture said method comprising culturing the stem cell in the presence of a defined medium supplemented with essential minerals selected from the group including Transferrin and Selenium, small molecules selected from the group including SB203580 and PGI2 and protein growth factors of the FGF, IGF and BMP families such as but not limited to IGF1, FGF2, BMP2, BMP4 and BMP6, a homologue or functional equivalent thereof. Desirably, insulin or an analogue is depleted from the media to progress the differentiation to cardiomyocytes.

In another aspect the invention also provides for improving yield of cardiomyocytes and cardiac progenitors by adopting the methods described herein.

The present invention also provides cardiomyocytes and cardiac progenitors prepared by the methods according to the present invention.

The present invention also provides transgenic cardiomyocytes and cardiac progenitors as well as enriched transgenic cardiomyocyte populations and cardiac progenitor populations prepared by the methods of the present invention.

The present invention further provides a cell composition including a differentiated cell of the present invention, and a carrier.

In another aspect the invention includes a method of repairing cardiac tissue, the method including transplanting an isolated cardiomyocyte or cardiac progenitor cell of the invention into damaged cardiac tissue of a subject.

In yet another aspect, the invention provides a myocardial model and methods for testing an effect of a compound on cardiomyocytes and cardiac progenitors.

FIGURES

DETAILED DESCRIPTION OF THE INVENTION

Figure 1:
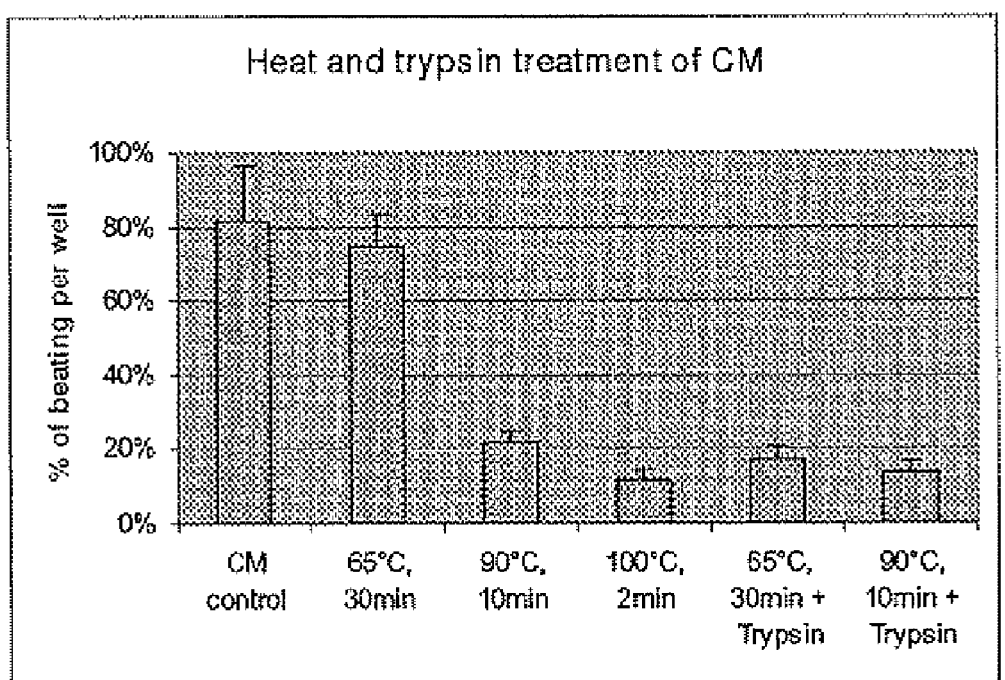
FIG. 1 shows the effect of heat and trypsin treatment on END2-CM.

The present invention provides a method of inducing or enhancing the induction of differentiation of stem cells, in particular hES cells, into cardiomyocytes or cardiac mesoderm by culturing the ES cells in the presence of a defined medium or chemically defined medium that is substantially free of xeno- and serum-components and thus comprises a clinically compliant medium. The defined media or chemically defined media comprises defined factors that contribute to the promotion of differentiation to cardiomyocytes or cardiac mesoderm.

A surprisingly efficient differentiation process is now provided in a defined medium that shows equivalent cardiomyocyte inducing properties as END2-CM. One example of such fully defined medium formulation provided in this embodiment is termed defined serum free medium or bSFS. As part of the process, culture conditions are provided that are useful to maintain human embryonic stem cells in a state that promotes efficient cardiomyocyte differentiation.

In a first aspect of the present invention there is provided a method of inducing cardiomyocyte differentiation of a human stem cell, the method comprising culturing the stem cell in the presence of a prostaglandin, analogue or functional equivalent thereof alone or in combination with other factors described herein such as essential minerals selected from the group including transferrin and selenium, small molecules selected from the group including a p38 MAPK inhibitor such as SB203580 and protein growth factors of the FGF, IGF and BMP families such as but not limited to IGF1, FGF2, BMP2, BMP4 and BMP6, a homologue or functional equivalent thereof. The prostaglandin, analogue or functional equivalent thereof may be prostacyclin (PGI2), an analogue or functional equivalent thereof, including its naturally breakdown form of 6-keto-Prostaglandin F1α (6k-PGF1α) and 2,3-dinor-6-keto-Prostaglandin F1α (2,3d-6k-PGF1α); its synthetic analogs, such as iloprost, cicaprost, and carbaprostacyclin (cPGI) and stable chemical structures (Whittle, 1980, Town, 1982, Sturzebecher, 1986); and its derivatives. The term prostanoids also includes prostaglandins, such as prostacyclins, thromboxanes, and related substances, but "prostaglandins" is often used loosely to include all prostanoids, Accordingly the invention also includes prostanoids within its scope.

Therefore not wishing to be limited by theory, functional equivalents may also include PGA, PGB, PGC, PGD (PGD2), PGE (PGE2), PGF (PGF2a), PGI (PGI2 as exemplified), Thromboxane A2 and 12(s)-HHT. These would also include the Amide and Ester Prostanoid derivatives.

Cardiomyocyte differentiation has been demonstrated in hES cells co-cultured with visceral endoderm-like cells (END2). Serum-free END2 conditioned media (END2-CM) from these cells exhibits an ability to induce cardiomyocyte differentiation of the hES cell lines.

Prostaglandins have now been found to assist in the differentiation of cardiomyocytes. In particular, by adding a Prostaglandin, analogue or functional equivalent thereof to a stem cell culture, cardiomyocyte differentiation may be enhanced over base line differentiation levels. For instance, where cardiomyocyte differentiation of stem cells is spontaneous or is induced under specific cardiomyocyte differentiation inducing conditions, the level of cardiomyocyte differentiation from stem cells to cardiomyocytes or cardiac progenitors can be increased resulting in increased numbers of cardiomyocytes and cardiac progenitors.

It is also conceivable for the present invention to include the use of a Prostaglandin, analogue or functional equivalent thereof to induce cardiomyocyte differentiation from an undifferentiated hES cell population that is capable of differentiation to cardiomyocytes and cardiac progenitors and preferably to direct and induce the differentiation toward a cardiomyocyte lineage.

The addition of a Prostaglandin, analogue or functional equivalent thereof is applicable to any method that is directed to differentiation of stem cells to cardiomyocytes or cardiac progenitors including both directed and spontaneous cardiomyocyte differentiation.

The Prostaglandin, analogue or functional equivalent thereof may be introduced at any stage of the culture. Ideally the Prostaglandin, analogue or functional equivalent thereof may be present continuously from the initial stage of culture of a stem cell or may be part of a co-culture of the stem cells.

In another embodiment the culturing conditions are serum-free conditions. The periods in which the conditions are serum free are ideally from the time of culture of the stem cells or as part of the co-culture of the stem cells.

The period over which cardiomyocyte differentiation is induced may be at least 6 days. The period may be 6 to 12 days. The concentration of the serum may therefore be changed over this period. For instance some of the period may be in the presence of serum, and the remaining period may be in the absence of serum. Ideally the period is serum free.

The serum-free conditions are most desired as the serum-free growth itself improves the efficiency of cardiomyocyte differentiation, beating areas being detected earlier and at higher frequency than under standard serum-containing conditions. However, the addition of a prostaglandin, analogue or functional equivalent thereof can improve or enhance the cardiomyocyte differentiation in substantially serum-free conditions. Hence in those conditions where serum may be present, it is within the spirit of the invention to use a prostaglandin, analogue or functional equivalent thereof to improve or enhance the cardiomyocyte differentiation.

The contents of WO2005/1181784 are herein incorporated by reference as the application describes the culturing of hES cells in serum free media.

Prostaglandin I2 (PIG2)

Prostaglandin I2 (prostacyclin) has now been identified as a preferred inducing factor alone or in combination with several growth factors and small molecules which may act as inducing or enhancing factors to direct and induce differentiation of human stem cells into cardiomyocytes and cardiac progenitors. The discovery of PGI2 as the inducing factor in CA is a critical one since the process of generating cardiomyocytes from hES cells can be made GMP. CM from a mouse cell line is no longer necessary, which is considered to be a xeno product and troublesome from a regulatory perspective.

Prostacyclin is an unstable prostaglandin released by mast cells and endothelium and is mainly synthesized by vascular endothelium and smooth muscle. It is a potent inhibitor of platelet aggregation and also causes vasodilation and increased vascular permeability. Release of PGI2 is enhanced by bradykinin. However, this compound has not been previously associated with the process of cardiomyocyte differentiation nor the induction of that process.

Whilst PGI2 has been found to be an inducing factor for cardiomyocyte differentiation, analogues of PGI2 such as but not limited to Beraprost, clinprost and PGI1-Na are also included in the present invention. Any one of the analogues that are commonly available is within the scope of the present invention. The analogue may be a stable analogue that is capable of prolonged culture. It must be suitable for inclusion into media for the cardiomyocyte induction.

The term "functional equivalent" also includes those compounds that can behave in the same manner and essentially act like PGI2.

The present invention also includes the addition of components that form PGI2. For instance, PGI2 is derived from arachidonic acid and produced by the cyclooxygenase (COX) system. Arachidonic acid, is first converted to PGH2 by prostaglandin-endoperoxide synthase (Ptgs or Cox1), and PGH2 is subsequently converted to PGI2 by the action of prostacyclin synthase (Ptgis). Therefore any of the compounds that contribute to the generation of PGI2 in culture are also included in the scope of the present invention.

In another embodiment the present invention provides a method for enhancing cardiomyocyte differentiation of a stem cell the method comprising co-culturing the stem cell with another cell or an extracellular medium of the cell culture, under cardiomyocyte or cardiac progenitor differentiating conditions in the presence of a prostaglandin, analogue or functional equivalent thereof.

The present invention provides a method to improve current culturing methods for the differentiation of cardiomyocytes by improving induction of differentiation. Hence "enhancing cardiomyocyte differentiation" can include increasing the number of cardiomyocytes differentiated in a culture compared with a culture that is not enhanced and improving the efficiency of the cardiomyocyte differentiation process. Hence the induction of differentiation is improved over baseline levels. "Enhancing" can also include inducing the cardiomyocyte from an undifferentiated stem cell culture that is capable of cardiomyocyte differentiation.

The methods of "enhancing" and "inducing" cardiomyocytes and cardiac progenitor differentiation results in increased yields of cardiomyocytes and cardiac progenitors from a culture of stem cells. Accordingly the present invention provides methods to improve the yield or total cell count of cardiomyocytes and cardiac progenitors from a culture to give rise to enriched populations of cardiomyocytes and cardiac progenitors from a stem cell culture.

Whilst the invention seeks to provide a culture system absent of xenoproducts, a co-culture system may be improved by improving the co-cultured cells as providing inducers of cardiomyocyte differentiation. Accordingly, methods to enhance PGI2 release from the cells are within the scope of the present invention. Hence, the co-cultured cells such as endothelial cells may be modified to induce the release of inducers such as PGI2, possibly by the use of compounds such as bradykinin.

Similarly, co-cultured cells may be genetically modified to increase PGI2 release wherein activating enzymes such as prostaglandin endoperoxidase synthase (Ptgs or Cox) and prostacyclin synthase (Ptgis) in the presence of arachidonic acid are further up-regulated to increase PGI2 release.

The concentration of PGI2, an analogue or functional equivalent thereof may be present in a range of 2 nM to 2000 nM, although a concentration of PGI2 in the range of 20 nM to 200 nM will also work well. However, these amounts closely approximate the effect on induction of cardiomyocyte differentiation that conditioned media has on the cells. The concentration of the pGI2 in the media is most desirably 20 nM.

The present invention also provides for the use of PGI2, an analogue or functional equivalent thereof for the induction of cardiomyocyte differentiation.

Inducing Cardiomyocyte Differentiation

The term "inducing cardiomyocyte differentiation" as used herein is taken to mean causing a human stem cell to develop into a cell of the cardiac lineage as a result of a direct or intentional influence on the stem cell. Influencing factors that may induce differentiation in a stem cell can include cellular parameters such as ion influx, a pH change and/or extracellular factors, such as secreted proteins, such as but not limited to growth factors and cytokines that regulate and trigger differentiation. Cells of the cardiac lineage include, but are not limited to cardiomyocytes and cardiac progenitors.

Stem Cells

In the present invention a human stem cell is undifferentiated prior to culturing and is capable of undergoing differentiation. The stem cell may be selected from the group including, but not limited to, embryonic stem cells, pluripotent stem cells, haematopoietic stem cells, totipotent stem cells, mesenchymal stem cells, neural stem cells, or adult stem cells.

The stem cell is ideally a human embryonic stem cell which may be derived directly from an embryo or from a culture of embryonic stem cells. For example, the stem cell may be derived from a cell culture, such as human embryonic stem cells (hES) cells (Reubinoff et al., *Nature Biotech.* 16:399-404 2000). The stem cell may be derived from an embryonic cell line or embryonic tissue. The embryonic stem cells may be cells which have been cultured and maintained in an undifferentiated state. Such cells have been described in WO2000/027995, WO20011042421, WO2001/098463 and WO2001/068815, the contents of which are incorporated herein by reference.

The stem cells suitable for use in the present methods may be derived from a patient's own tissue. This would enhance compatibility of differentiated tissue grafts derived from the stem cells with the patient. The stem cells may be genetically modified prior to use through introduction of genes that may control their state of differentiation prior to, during or after their exposure to PGI2, an analogue or functional equivalent thereof. They may be genetically modified through introduction of vectors expressing a selectable marker under the control of a stem cell specific promoter such as Oct-4 or of genes that may be upregulated to induce cardiomyocyte differentiation. The stem cells may be genetically modified at any stage with markers or gene so that the markers or genes are carried through to any stage of culturing. The markers may be used to purify or enrich the differentiated or undifferentiated stem cell populations at any stage of culture.

It is expected that these culture conditions for improved or enhanced cardiomyocyte differentiation will be applicable at least to all stem cell lines from the same sources as those tested and suggested that these culture conditions for improved cardiomyocyte differentiation are applicable to all stem cell lines and stem cells in general. Furthermore, the fact that these differentiation conditions can be established without fetal calf serum, and thus without the potential presence of animal pathogens, increases the chance that these hES-derived cardiomyocytes are suitable for cardiomyocyte transplantation in patients with cardiac disease.

Culture Media and Prostaglandins

In another aspect of the present invention, there is provided a culture media when used for the induction of cardiomyocyte differentiation in stem cells, said media comprising a prostaglandin, analogue or functional equivalent thereof alone or in combination with other factors described herein such as essential minerals selected from the group including Transferrin and Selenium, small molecules selected from the group including a p38 MAPK inhibitor such as SB203580 and protein growth factors of the FGF, IGF and BMP families such as but not limited to IGF1, FGF2, BMP2, BMP4, and BMP6, a homologue or functional equivalent thereof. Preferably, the prostaglandin, analogue or functional equivalent thereof is prostacyclin (PGI2), an analogue or functional equivalent thereof as herein described.

It is intended that the culture media is capable of delivering a final concentration of the prostacyclin (PGI2), an analogue or functional equivalent thereof to a culture of stem cells in the range of 2 nM to 2000 nM. A final concentration in the range of 20 nM to 200 nM is desired. A person skilled in the art will appreciate that a suitable concentration can be determined by suitable trial and experimentation given the above amounts.

The culture media may be any media that supports stem cell differentiation. Ideally, the media is a DMEM based media and it may be supplemented with growth factors, small molecules and essential minerals including β-ME, non-essential amino acids, L-glutamine, Transferrin and Selenium. However, it is best to induce cardiomyocyte differentiation in a serum free media. It is also ideal that insulin is not present in the media or is at least reduced, ideally to below 10 ng/ml and is most desirably absent. The media may be supplemented with Transferrin and Selenium. The small molecules may include SB203580 and PGI2. Growth factors may be of the FGF, IGF and BMP families including IGF-1, FGF-2 and BMP2, BMP4 and BMP6. Further additives may include retinoic acids acetic acid, hydrogen peroxide and bone morphogenic protein.

The invention also provides use of serum free medium containing a prostaglandin, analogue or functional equivalent thereof for use in a method of inducing differentiation of stem cells into cardiomyocytes and cardiac progenitors. The media may be supplemented with growth factors, small molecules and essential minerals including β-ME, non-essential amino acids, L-glutamine, Transferrin and Selenium.

Genomic Analysis

In another aspect of the present invention there is provided a method of inducing cardiomyocyte differentiation of a stem cell, the method comprising culturing the cells in the presence of a gene product expressed by the END2 cell line.

The gene product may be expressed from a gene listed in Table 1. These genes represent soluble and secreted factors produced by a cell that has been co-cultured with a hES cell when cardiomyocyte differentiation has been induced. Without being limited by theory, it is postulated that the genes that are up-regulated and result in cardiomyocyte differentiation are associated with an activity that contributes to the end result of cardiomyocyte differentiation.

TABLE 1

| Gene symbol | GenBank Accession | Description |
| --- | --- | --- |
| Slit3 | AF144629 | Slit homolog 3 (*Drosophila*) |
| Colec11 | AK003121 | Collectin sub-family member 11 |
| Prlpn | AK005458 | Prolactin-like protein N |
| Crim1 | AK034889 | Cysteine-rich motor neuron 1 |
| IGF1 | AK050118 | Insulin-like growth factor 1 |
| 9330129D05Rik | AK080793 | RIKEN cDNA 9330129D05 gene |
| Igfbp4 | AK081766 | Insulin-like growth factor binding protein 4 |
| Igfbp5 | BC003951 | Insulin-like growth factor binding protein 5 |
| Atrnl1 | BC030872 | RIKEN cDNA E430018L07 gene |
| Mmrn1 | BC046425 | Multimerin 1 |
| Il18 | BU700305 | Interleukin 18 |
| Pace4 | D50060 | Paired basic amino acid cleaving system 4 |
| Msln | D86370 | Mesothelin |
| H2-K1 | M13200 | Histocompatibility 2, K1, K region |
| 2610507B11Rik | NM_001002004 | RIKEN cDNA 2610507B11 gene |
| Pzp | NM_007376 | Pregnancy zone protein |
| Bmp4 | NM_007554 | Bone morphogenetic protein 4 |
| Bmp6 | NM_007556 | Bone morphogenetic protein 6 |
| Col5a2 | NM_007737 | Procollagen, type V, alpha 2 |
| Col1a1 | NM_007742 | Procollagen, type I, alpha 1 |
| Col1a2 | NM_007743 | Procollagen, type I, alpha 2 |
| Efna2 | NM_007909 | Ephrin A2 |
| Epx | NM_007946 | Eosinophil peroxidase |
| H2-D4 | NM_008200 | Histocompatibility 2, D region locus 4 |
| Hdgf | NM_008231 | Hepatoma-derived growth factor |
| Igfbp2 | NM_008342 | Insulin-like growth factor binding protein 2 |
| Igfbp3 | NM_008343 | Insulin-like growth factor binding protein 3 |
| Igfbp6 | NM_008344 | Insulin-like growth factor binding protein 6 |
| Ins2 | NM_008387 | Insulin II |
| Lif | NM_008501 | Leukemia inhibitory factor |
| Ltbp3 | NM_008520 | Latent transforming growth factor beta binding protein 3 |
| Mest | NM_008590 | Mesoderm specific transcript |
| Mmp2 | NM_008610 | Matrix metalloproteinase 2 |
| Naga | NM_008669 | N-acetyl galactosaminidase, alpha |
| Ngp | NM_008694 | Neutrophilic granule protein |
| Nid2 | NM_008695 | Nidogen 2 |
| Ntf3 | NM_008742 | Neurotrophin 3 |
| Nxph1 | NM_008751 | Neurexophilin 1 |
| Cntn3 | NM_008779 | RIKEN cDNA 4930587E11 gene |
| C130009A20Rik | NM_008858 | RIKEN cDNA C130009A20 gene |
| Aldh1a2 | NM_009022 | Aldehyde dehydrogenase family 1, subfamily A2 |
| Scgf | NM_009131 | Stem cell growth factor |
| Sema3a | NM_009152 | Sema domain, immunoglobulin domain (Ig), short basic domain secreted, (semaphorin) 3A |
| Sepp1 | NM_009155 | Selenoprotein P, plasma, 1 |
| Tnfaip6 | NM_009398 | Tumor necrosis factor alpha induced protein 6 |
| Wnt11 | NM_009519 | Wingless-related MMTV integration site 11 |
| Wnt3 | NM_009521 | Wingless-related MMTV integration site 3 |
| Wnt5a | NM_009524 | Wingless-related MMTV integration site 5A |
| Wnt5b | NM_009525 | Wingless-related MMTV integration site 5B |
| Agpt4 | NM_009641 | Angiopoietin 4 |
| Apoe | NM_009696 | Apolipoprotein E |
| Glb1 | NM_009752 | RIKEN cDNA C130097A14 gene |
| Brca1 | NM_009764 | Breast cancer 1 |
| Serping1 | NM_009776 | Serine (or cysteine) proteinase inhibitor, clade G, member 1 |
| C3 | NM_009778 | Complement component 3 |
| Chi3l3 | NM_009892 | Chitinase 3-like 3 |
| Col3a1 | NM_009930 | Procollagen, type III, alpha 1 |
| Col4a2 | NM_009932 | Procollagen, type IV, alpha 2 |
| Ctsc | NM_009982 | Cathepsin C |
| Dkk1 | NM_010051 | Dickkopf homolog 1 (*Xenopus laevis*) |
| Edn1 | NM_010104 | Endothelin 1 |
| D330023I04Rik | NM_010181 | RIKEN cDNA D330023I04 gene |
| Fgf14 | NM_010201 | Fibroblast growth factor 14 |
| Fgf5 | NM_010203 | Fibroblast growth factor 5 |
| Fgf8 | NM_010205 | Fibroblast growth factor 8 |
| Fn1 | NM_010233 | Fibronectin 1 |
| Hexa | NM_010421 | Hexosaminidase A |

TABLE 1-continued

| Gene symbol | GenBank Accession | Description |
|---|---|---|
| Hs3st1 | NM_010474 | Heparan sulfate (glucosamine) 3-O-sulfotransferase 1 |
| Igf1 | NM_010512 | Insulin-like growth factor 1 |
| Igf2 | NM_010514 | Insulin-like growth factor 2 |
| Cyr61 | NM_010516 | Cysteine rich protein 61 |
| Klrd1 | NM_010654 | Killer cell lectin-like receptor, subfamily D, member 1 |
| Mdk | NM_010784 | Midkine |
| Pdgfb | NM_011057 | Platelet derived growth factor, B polypeptide |
| Plod1 | NM_011122 | Procollagen-lysine, 2-oxoglutarate 5-dioxygenase 1 |
| Saa4 | NM_011316 | Serum amyloid A 4 |
| Sema3f | NM_011349 | Sema domain, immunoglobulin domain (Ig), short basic domain secreted, (semaphorin) 3 F |
| Frzb | NM_011356 | Frizzled-related protein |
| Agr2 | NM_011783 | Anterior gradient 2 (*Xenopus laevis*) |
| Plod2 | NM_011961 | Procollagen lysine, 2-oxoglutarate 5-dioxygenase 2 |
| Aldh1a1 | NM_013467 | RIKEN cDNA E030003E18 gene |
| Fgf9 | NM_013518 | Fibroblast growth factor 9 |
| Gdf6 | NM_013526 | Growth differentiation factor 6 |
| Tcn2 | NM_015749 | Transcobalamin 2 |
| Hs6st1 | NM_015818 | Heparan sulfate 6-O-sulfotransferase 1 |
| Reck | NM_016678 | Reversion-inducing-cysteine-rich protein with kazal motifs |
| Pgcp | NM_018755 | Plasma glutamate carboxypeptidase |
| Prss11 | NM_019564 | Protease, serine, 11 (Igf binding) |
| Cpxm1 | NM_019696 | Carboxypeptidase X 1 (M14 family) |
| Nme3 | NM_019730 | Expressed in non-metastatic cells 3 |
| Ctsf | NM_019861 | Cathepsin F |
| Pdgfc | NM_019971 | Platelet-derived growth factor, C polypeptide |
| Fgf21 | NM_020013 | Fibroblast growth factor 21 |
| Smpdl3a | NM_020561 | Sphingomyelin phosphodiesterase, acid-like 3A |
| Ckb | NM_021273 | Creatine kinase, brain |
| Ntn4 | NM_021320 | Netrin 4 |
| Fmod | NM_021355 | Fibromodulin |
| Agrn | NM_021604 | Agrin |
| Wnt2 | NM_023653 | Wingless-related MMTV integration site 2 |
| 1500015O10Rik | NM_024283 | RIKEN cDNA 1500015O10 gene |
| Rarres2 | NM_027852 | Retinoic acid receptor responder (tazarotene induced) 2 |
| Tmem25 | NM_027865 | Transmembrane protein 25 |
| Aldh1b1 | NM_028270 | Aldehyde dehydrogenase 1 family, member B1 |
| Mfap4 | NM_029568 | Microfibrillar-associated protein 4 |
| 1810049K24Rik | NM_030209 | RIKEN cDNA 1810049K24 gene |
| C1qtnf3 | NM_030888 | C1q and tumor necrosis factor related protein 3 |
| Col2a1 | NM_031163 | Procollagen, type II, alpha 1 |
| Nxph3 | NM_130858 | Neurexophilin 3 |
| Chrdl2 | NM_133709 | Chordin-like 2 |
| Smpdl3b | NM_133888 | Sphingomyelin phosphodiesterase, acid-like 3B |
| D10Jhu81e | NM_138601 | DNA segment, Chr 10, Johns Hopkins University 81 expressed |
| Anapc2 | NM_175300 | Anaphase promoting complex subunit 2 |
| Egfl7 | NM_178444 | EGF-like domain 7 |
| Prss35 | NM_178738 | Protease, serine, 35 |
| Lama5 | U37501 | Laminin, alpha 5 |
| Kitl | U44725 | Kit ligand |

The gene product may also be expressed from a gene selected from the group consisting of Bmp6, Fgf9, Bmp4, Scf, Igf2, Ptgis and Ptgs1, These genes will encode for gene products that affect and induce cardiomyocyte differentiation.

The gene product may be selected from the group consisting of Fgf9, Bmp6, Bmp4, Scf, Igf2, Ptgis and Ptgs1. Applicants have found that by introducing any one or more of these compounds or a compound that is a product of their enzyme activity to a culture of stem cells that cardiomyocyte differentiation is increased. The addition Ptgis and Ptgs1 in combination with arachidonic acid may induce cardiomyocyte differentiation. It is considered that the introduction of these gene products may in combination with arachidonic acid result in the formation of PGI2 which has been found to be a cardiomyocyte differentiation inducer.

It is also conceivable that cells may be genetically modified to incorporate any one or more of the genes that are over-expressed and which may be involved in the induction of cardiomyocyte differentiation. Accordingly, the invention also provides for genetically modified cells or stem cells that harbour any one or more of the genes from Table 1 and most preferably any one or more of the genes selected from the group consisting of Bmp6, Fgf9, Bmp4, Scf, Bmp6, Igf2, Ptgis and Ptgs1 that can be up- or down-regulated.

If these genes can be induced to be up-regulated in a stem cell of the present invention, cardiomyocyte differentiation may be induced intrinsically in the stem cells.

Culture Media and Expressed Gene Products

In yet another aspect of the present invention there is provided a culture media when used for the induction of cardiomyocyte differentiation in stem cells, said media comprising a gene product expressed from a gene listed in Table 1. The gene product may be expressed from a gene selected from the group consisting of Bmp6, Fgf9, Bmp4, Scf, Igf2, Ptgis and Ptgs1. Ideally the culture media includes a gene product selected from the group consisting of Fgf9, Bmp6, Bmp4, Scf, Igf2, Ptgis and Ptgs1 alone or in combination.

In another aspect of the invention there is provided a culture media when used for the induction of cardiomyocyte differentiation in stem cells, said media comprising Fgf9, Bmp6, Bmp4, Scf, Igf2, Ptgis or Ptgs1 alone or in combination.

In yet another aspect, the present invention includes a culture media when used for the induction of cardiomyocyte differentiation in stem cells, said media comprising any one of Fgf9, Bmp6, Bmp4, Scf, Igf2, Ptgis or Ptgs1 in combination with a prostaglandin such as PGI2.

The culture media which includes the gene products may also include other factors that can enhance the induction of cardiomyocyte differentiation such as essential minerals selected from the group including Transferrin and Selenium, small molecules selected from the group including a p38 MARK inhibitor such as SB203580 and protein growth factors of the FGF, IGF and BMP families such as but not limited to IGF1, FGF2, BMP2, BMP4 and BMP6, a homologue or functional equivalent thereof. Further additives may be present such as retinoic acid, acetic acid, hydrogen peroxide and bone morphogenic protein.

Enhancing Induction of Cardiomyocyte Differentiation

In another aspect of the present invention there is provided a method of further enhancing induction of cardiomyocyte differentiation from a co-culture of a stem cell and an embryonic cell, said method comprising further inducing expression of a gene product expressed by a gene listed in Table 1. The gene product may be expressed by a gene selected from the group consisting of Bmp6, Fgf9, Bmp4, Scf, Igf2, Ptgis and Ptgs1. The gene product may be selected from the group consisting of Fgf9, Bmp6, Bmp4, Scf, Igf2, Ptgis and Ptgs1. The gene product may be further expressed by a gene of the embryonic cell.

In another aspect of the invention there is provided a method of further enhancing induction of cardiomyocyte differentiation said method comprising culturing the stem cell and conditioned media from a culture of an embryonic cell, in the presence of a gene product expressed by END2 cells. The gene product may be expressed by a gene listed in Table 1. The gene product may be expressed by a gene selected from the group consisting of Bmp6, Fgf9, Bmp4, Scf, Igf2, Ptgis and Ptgs1. The gene product may be selected from the group consisting of Fgf9, Bmp6, Bmp4, Scf, Igf2, Ptgis and Ptgs1.

In yet another aspect there is provided a method of further enhancing induction of cardiomyocyte differentiation said method comprising culturing the stem cell and conditioned media from a culture of an embryonic cell, in the presence of any one of Fgf9, Bmp6, Bmp4, Scf, Igf2, Ptgis or Ptgs1 alone or in combination. Here these products need not be expressed by a gene but may be synthetically produced for inclusion into the media. The method may further include culturing the stem cells in the presence of a prostaglandin such as PGI2.

Applicants have found that the genes listed in Table 1 are expressed in co-cultured cells such as visceral endoderm cells when cardiomyocyte differentiation is induced. Adding these components to END2 conditioned media further enhances the induction of cardiomyocyte differentiation and increases the number of beating areas. Hence any one or more of these components may be used as inducers of cardiomyocyte differentiation.

Progressing Cardiomyocyte Differentiation

In another aspect of the present invention there is provided a method of enabling cardiomyocyte differentiation in a stem cell culture said method comprising reducing an effect caused by insulin or an analogue thereof on the stem cell in culture.

It has now been found that media depleted of insulin is permissive for cardiomyocyte formation. As the media is conditioned by the END2 cells the insulin levels decrease. This low concentration of insulin containing conditioned media is then added to the stem cells that are then allowed to differentiate. Accordingly, without being limited by theory, the depletion of insulin and possibly other inhibitory factors allows or permits the stem cells to progress toward differentiation to a cardiomyocyte lineage.

A marked reduction in insulin concentration was noted which coincided with ability of END2-CM to induce of cardiomyocyte differentiation. Insulin therefore affects the progression of the cell toward the cardiomyocyte lineage and this has been found in the examples whereby spiking insulin back into END2 conditioned media which can induce cardiomyocyte differentiation, the progression toward cardiac differentiation is severely inhibited. Accordingly, insulin affects the differentiation directly or indirectly. Hence it is within the scope of the invention that to progress the stem cell toward cardiac differentiation, it is preferred to reduce the inhibitory effect caused by insulin by depleting insulin from the culture media. However, where insulin is not present in a culture media, the induction of cardiomyocyte differentiation may be progressed by alleviating equivalent effects caused by insulin analogues or functional equivalents.

Suitable insulin analogues include Lispro or Aspart or Glargine Insulin and any other suitable analogue.

There is also provided a method of enabling cardiomyocyte differentiation in a stem cell culture said method comprising culturing the stem cell in the presence of a defined medium supplemented with essential minerals selected from the group including transferrin and selenium, small molecules selected from the group including SB203580 and PGI2 and protein growth factors of the FGF, IGF and BMP families selected from IGF1, FGF2, BMP2, BMP4 and BMP6, a homologue or functional equivalent thereof. This may be used in combination with the removal of insulin and the effects caused by insulin.

The present invention also provides for the use of insulin or an analogue thereof for the inhibition of induction of cardiomyocyte differentiation in stem cells. The introduction of insulin abrogates cardiomyocyte differentiation. Any amount of insulin or an analogue can impact on the induction of cardiomyocyte differentiation.

Cardiomyocytes, Cardiac Progenitors and Cardiomyocyte Cell Compositions

The present invention also provides cardiomyocytes and cardiac progenitors prepared by the methods according to the present invention and outlined herein. The cardiomyocytes and cardiac progenitors may be genetically modified with reporter genes or with genes listed in Table 1. The reporter genes can assist in the selection of the cardiomyocytes and cardiac progenitors.

The cardiomyocytes and cardiac progenitors of the invention may be beating. Cardiomyocytes and the cardiac progenitors can be fixed and stained with α-actinin antibodies to confirm muscle phenotype. α-troponin, α-tropomysin and α-MHC antibodies also give characteristic muscle staining.

The present invention also provides a mutated differentiated cardiomyocyte or cardiac progenitor of the invention prepared from a mutant stem cell. It will be recognized that methods for introducing mutations into cells are well known in the art. Mutations encompassed are not only mutations resulting in the loss of a gene or protein but also those causing over expression of a gene or protein.

The present invention further provides a cell composition including a differentiated cell of the present invention, and a carrier. The carrier may be any physiologically acceptable carrier that maintains the cells. It may be PBS or other minimum essential medium known to those skilled in the field. The cell composition of the present invention can be used for biological analysis or medical purposes, such as transplantation.

The cell composition of the present invention can be used in methods of repairing or treating diseases or conditions, such as cardiac disease or where tissue damage has occurred. The treatment may include, but is not limited to, the administration of cells or cell compositions (either as partly or fully differentiated) into patients. These cells or cell compositions would result in reversal of the condition via the restoration of function as previously disclosed above through the use of animal models.

Methods of Use

The present invention also provides differentiated cells produced using methods of the invention that may be used for transplantation, cell therapy or gene therapy. Ideally, the invention provides a differentiated cell produced using methods of the invention that may be used for therapeutic purposes, such as in methods of restoring cardiac function in a subject suffering from a heart disease or condition.

Another aspect of the invention is a method of treating or preventing a cardiac disease or condition. Cardiac disease is typically associated with decreased cardiac function and includes conditions such as, but not limited to, myocardial infarction, cardiac hypertrophy and cardiac arrhythmia. In this aspect of the invention, the method includes introducing an isolated differentiated cardiomyocyte cell of the invention and for a cell capable of differentiating into a cardiomyocyte cell when treated using a method of the invention into cardiac tissue of a subject. The isolated cardiomyocyte cell may be transplanted into damaged cardiac tissue of a subject. Ideally, the method results in the restoration of cardiac function in a subject.

In yet another aspect of the invention there is provided a method of repairing cardiac tissue, the method including introducing an isolated cardiomyocyte or cardiac progenitor cell of the invention and for a cell capable of differentiating into a cardiomyocyte cell when treated using a method of the invention into damaged cardiac tissue of a subject.

The subject may be suffering from a cardiac disease or condition. In the method of repairing cardiac tissue of the present invention, the isolated cardiomyocyte cell may be transplanted into damaged cardiac tissue of a subject. Ideally, the method results in the restoration of cardiac function in a subject.

The present invention may also provide a myocardial model for testing the ability of stem cells that have differentiated into cardiomyocytes to restore cardiac function.

The present invention preferably provides a myocardial model for testing the ability of stems cells that have differentiated into cardiomyocytes or cardiac progenitors using methods of the invention to restore cardiac function. In order to test the effectiveness of cardiomyocyte transplantation in vivo, it is important to have a reproducible animal model with a measurable parameter of cardiac function. The parameters used should clearly distinguish control and experimental animals [see for example in Palmen et al. (2001), Cardiovasc. Res. 50, 516-524] so that the effects of transplantation can be adequately determined. PV relationships are a measure of the pumping capacity of the heart and may be used as a read-out of altered cardiac function following transplantation.

A host animal, such as, but not limited to, an immunodeficient mouse may be used as a 'universal acceptor' of cardiomyocytes from various sources. The cardiomyocytes are produced by methods of the present invention.

The myocardial model of the present invention is preferably designed to assess the extent of cardiac repair following transplant of cardiomyocytes or suitable progenitors into a suitable host animal. The host animal may be an immunodeficient animal created as a model of cardiac muscle degeneration following infarct that is used as a universal acceptor of the differentiated cardiomyocytes. This animal may be any species including but not limited to murine, ovine, bovine, canine, porcine and any non-human primates. Parameters used to measure cardiac repair in these animals may include, but are not limited to, electrophysiological characteristic of heart tissue or various heart function. For instance, contractile function may be assessed in terms of volume and pressure changes in a heart. Preferably, ventricular contractile function is assessed. Methods of assessing heart function and cardiac tissue characteristics would involve techniques also known to those skilled in the field.

The present invention also provides a model for the study of human cardiomyocytes in culture, comprising differentiated cardiomyocytes or cardiac progenitors of the invention. This model is useful in the development of cardiomyocyte transplantation therapies.

Further, the present invention provides an in vitro system for testing cardiovascular drugs comprising a differentiated cardiomyocyte of the invention. The system can be used to test an effect of a compound on the cardiac activity of a cardiomyocyte or cardiac progenitor by subjecting the cardiomyocyte or cardiac progenitor to the test compound and measuring a parameter such as a physiological or electrophysiological effect caused by the test compound.

Throughout the description and claims of this specification, the word "comprise" and variations of the word, such as "comprising" and "comprises", is not intended to exclude other additives, components, integers or steps.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed in Australia before the priority date of each claim of this application.

The present invention will now be more fully described with reference to the accompanying examples and drawings. It should be understood, however that the description following is illustrative only and should not be taken in any way as a restriction on the generality of the invention described above.

EXAMPLES

Example 1

Characterization of END2 Conditioned Media

I. Materials and Methods
(i) Preparation of END2 Conditioned Medium

END2 cells secrete a factor into culture medium that can induce cardiomyocyte differentiation in hES cells. END2 conditioned media (END-CM) is defined as serum-free (SF) media that has been used to culture END-2 cells for four days or more and contains cardiomyocyte-inducing factor/s and/or bioactivity thereafter. hES cells are Human Embryonic Stem Cells. END2 cells are a visceral-endoderm-like cell line derived from P19, a mouse embryonal carcinoma cell line.

For the production of END2-CM END2 cells were seeded at a density of $1.4\times10^5$ cells/cm$^2$ in a T175 flask (Nunc) and were grown for about 3 days in Dulbecco's Modified Eagle's Medium (DMEM)/F12 media (Invitrogen) supplemented with 7.5% fetal calf serum (ECS; Hyclone) until confluency. The confluent END2 cell layer was washed once in PBS$^+$ (Gibco) and serum free (SF) medium was used for conditioning. SF medium is defined as DMEM supplemented with 1% MEM non-essential amino acids, 2 mM L-Glutamine, ITS (Insulin-Transferrin-Selenium), 0.1 mM β-mercaptoethanol and Penicillin/Streptomycin (all invitrogen). Around 200 μl of serum free DMEM per cm$^2$ of END2 growth area) was added to start the conditioning process.

The conditioning period ranged from 4 to 7 days. For harvest the medium was removed from the tissue culture flask and filtered with a disposable filtration system (0.22 μM, Millipore). The filtered END2-CM can be used immediately or stored at 4° C. or at −80° C. END2-CM can be prepared from END2 cells with passage numbers higher than 45 without loss of its cardiomyocyte inducing activity.

(ii) Culture of hES Cells on Feeder Cells hES cells (line hES2 and hES3-GFP) were grown on mouse embryonic feeder cells as published previously (Reubinoff, 2000 and Costa, 2005). In short, the hES cells were cultured in DMEM with 20% FCS, 0.1 mM β-mercaptoethanol, 1% MEM non-essential amino acids, 2 mM L-glutamine and antibiotics (Penicillin/Streptomycin) on Mitomycin C (10 μg/ml, Sigma) treated embryonic feeder cells.

Human fibroblastic feeder cells CCD-919Sk were obtained from ATCC(CRL-1826). Cells were cultured in T175 flasks in DMEM with 20% FCS, 2 mM L-Glutamine, Insulin-Transferrin-Selenium (ITS), FGF2 (10 ng/ml; Invitrogen) and antibiotics (Pen/Strep) to confluence and treated with Mitomycin C (10 μg/ml) for 3 hours. Cells were passaged with trypsin/EDTA (0.125% w/v; 50 mM respectively; Gibco) and seeded at a density of $4.7\times10^4$ cells/cm$^2$ in culture trays (Nunc). The CCD919Sk cells were equilibrated in hES culture medium for 24 h before the hES were seeded on the feeder cells.

hES cells on both feeder lines were subcultured by treating with Collagenase IV (Gibco) for 3 min and mechanical slicing of individual colonies. The cell clumps were then transferred to newly prepared feeder cells. Enzymatically passaged cells were discarded after 20 passages and cells maintained by mechanical passaging were newly adapted to collagenase passaging.

(iii) Embryoid Body Formation from Human Embryonic Stem Cells and Treatment with END2 Conditioned Medium This procedure describes the formation of embryoid bodies (EB) from collagenase-derived hES cell cultures. After formation the EBs were then exposed to END2 conditioned medium (CM). EB culture in CM over a period of 12 days induces cardiomyocyte differentiation in some of the EBs.

Enzymatically passaged hES cells grown on feeder cells were washed once with PBS$^+$ and treated with Collagenase IV (1 mg/ml) for 3-4 min at 37° C. The Collagenase IV solution was replaced by DMEM and the cells were mechanically dissociated with a pipette tip. Cells were then harvested using a cell scraper and the cell suspension was transferred to a 50 ml tube (Falcon). Cell clumps were collected by gravity and the supernatant was aspirated. Cells were resuspended in fresh DMEM medium aiming to uniformly disperse the cell clumps in the suspension. An equal volume of the cell suspension was then transferred to ultra low attachment plates (Costar). Usually 6-well plates were used and cells were cultured in 2 ml of medium. Alternatively, cells can be seeded into plates under conditions supporting cell adherence to induce differentiation of hES cells attached to a surface.

In suspension culture, EBs are formed in ultra low attachment plates in SF medium over night. After over night incubation SF medium was replaced by fresh SF medium or END2-CM respectively for further differentiation. Subsequent medium changes were performed every 3-4 days. Usually, cells were cultured over a period of 12-13 days before the visual analysis of the proportion of beating EBs under a microscope was performed followed by cell collection for additional readouts. Multiple beating areas on single EBs were not counted separately. Values are expressed as a percentage of contracting EBs compared to non-contracting EBs in a single well of a 6-well tray. Cell harvest and analysis at time points other then 12-13 days after EB formation is indicated in the respective examples and figures of this embodiment. For EB scoring and other analytical methods hES cell differentiation was performed in triplicates applying the same culture conditions (e.g. the same medium added) in 3 independent wells of a 6-well plate. An average value per well was calculated and presented.

Alternatively, EBs can also be formed by culturing hES directly in END2-CM or other suitable media without prior incubation in SF media over night. Different types of culture vessels that support cell cultivation in suspension culture such as Petri dishes, spinner flasks or other types of bioreactors might be used.

(iv) RT-PCR for Cardiac Markers

RNA extraction: EBs at the end of the twelve day period were harvested. EBs from 3 wells were pooled and washed once in PBS$^-$. Trizol (Invitrogen) was added before freezing the EBs at −80° C. to ease cell lysis. Frozen samples were thawed and harshly mixed. Chloroform was added to the sample and incubated for 3 min at room temperature. The sample was centrifuged for 15 min at 13000 rpm at 4° C. and the aqueous phase collected. An equal volume of 70% ethanol was added before the sample was loaded onto an RNeasy mini column (Qiagen). The column was centrifuged for 15 sec at $\geq 8000$ g. The rest of the purification steps were performed according to manufacturer's instructions. RNA was eluted in RNase-free water. 5 μg of the RNA sample was then treated with DNase (Invitrogen) in a volume of 50 μl. The mixture was incubated at room temperature for 30 min and heat inactivated for 10 min at 80° C. before cooling rapidly on ice.

(v) Reverse Transcriptase

5 μg of total RNA was mixed with 2 μl of 3 μg/μl random primers (Invitrogen) in a final volume of 100 μl. 75 μl were reversed transcribed (BioLabs), the remaining 25 μl served as a negative control. Samples were incubated for 1 hour at 37° C. before the reaction was terminated for 5 min at 95° C.

(iv) Real Time PCR

RT-PCR was performed using 100 ng of cDNA with the following conditions: Cycle 1 (40×) denaturation at 95° C. for 10 s, annealing at 58° C. for 30 s and extension at 72° C. for 45 s. Melting curve step was included at the end with the following conditions: Cycle 2 (80×) 55° C. for 10 s with setpoint temperature increased after cycle at 0.5° C. β-actin is served as an internal control. The gene primers used are α-MHC (sense primer: ATTGCTGAAACCGAGAATGG (SEQ ID NO: 1); antisense primer: CGCTCCTTGAGGT-TGAAAAG (SEQ ID NO: 2)), ANF (sense primer: TTACTGGCATTCCAGCTCCT (SEQ ID NO: 3); antisense primer (GGGCACGACCTCATCTTCTA (SEQ ID NO: 4)) and β-Actin (sense primer: CAATGTGGCCGAG- GACTTTG (SEQ ID NO: 5); antisense primer: CATTCTC-CTTAGAGAGAAGTGG (SEQ ID NO: 6)). All reactions were run in triplicate.

II. Characterization of END2 CM (i) END2 Conditioned Media Property Check

Day 4 END2 CM was subjected to following treatments:
fresh media with no treatment (control)
heat treatment (30 min, 65° C.): 4 ml aliquot heated in water bath
heat treatment (10 min, 90° C.): 4 ml aliquot heated in heat block
heat treatment (2 min, 100° C.): 4 ml aliquot heated in heat block
trypsin treatment: treating media 20 µg/ml trypsin for 2 hrs at 37° C., followed by addition of 40 µg/ml trypsin-inhibitor.
heat and trypsin treatment: heated the CM as above, cooled to room temperature and followed by trypsin treatment as above.

(ii) Size Fractionation of END2 CM

Size fractionation of CM was done using centrifugal columns Centriplus YM-3 (Millipore, USA) with molecular cut-off of 3000 K Da. Briefly, freshly collected END2 CM (10-15 ml) were added to the columns, and centrifuged at 3000 g at 4° C. until around 0.5-1 ml of the retentate was left. Typically, it takes 5-6 hr for a starting volume of 15 ml. After centrifugation, the filtrate (pass-through) was collected and filtered with 0.22 µM low-binding filter and used as culture media designated as "3 k lower". Stirred Ultrafiltration Cell Models 8400 (Millipore) with Ultrafiltration membrane with Molecular size cut-off 500 Da were used to filter CM to obtain a 500 Da lower fraction according to the Millipore User Guide III. Media Components Analysis The SF medium refers to DMEM supplemented with 1% MEM non-essential amino acids, 2 mM L-Glutamine, ITS (Insulin-Transferrin-Selenium), 0.1 mM β-mercaptoethanol and Penicillin/Streptomycin (all Invitrogen). The DMEM3 medium refers to DMEM supplemented with 1% MEM non-essential amino acids, 2 mM L-Glutamine, and Penicillin/Streptomycin. DMEM refers to DMEM media alone.

(i) END2 CM Serial Dilution

END2 Day 4 CM was serially diluted by the addition of various percentages (as indicated in the results) of SF and DMEM before using it for culturing of hES cells as EBs.

(ii) Insulin Spiked into END2-CM

Insulin (Roche) at final concentration of 0.1-10 ug/ml, added into END2-CM respectively during every medium change.

(iii) Insulin ELISA Assay:

Insulin concentration in the SF medium or END2-CM medium was determined by a Human Insulin ELISA kit (Lincon Research: cat# EZHI-14K) and was used according to the manual's instruction. The insulin concentrations were calculated based on the standard curve prepared at concentration of 0.08, 0.2, 0.4, 0.8, 2, 4, and 8 ng/ml.

VI. Cardiomyocyte Inducing Factor Property Check of Protein-Based Activity of END2-CM To characterize the physiochemical properties of inducing activity produced by END2 cells, the END2-CM was subjected to heat and trypsin treatment and evaluated by its induction activity in an aim to define whether the inducing factor is protein-based. The percentage of beating areas was scored at day 12. As showed in FIG. 1 the END2 factor seems stable at 65° C. treatment for 30 min.

Beating was also observed and scored at day 12 with a decrease in the of number of beating areas in heat treated CM at higher temperature (90° C.-100° C.) followed by protease (trypsin) digestion, which due to the harsher treatment presumably denatured and/or degraded almost all the proteins. This remaining cardiomyocyte inducing activity indicates that the biological activity of the inducing factor produced by END2 cells could not be completely abrogated by protease and heat treatment and therefore at least some components responsible for the bioactivity may not be protein-based.

Figure 2:
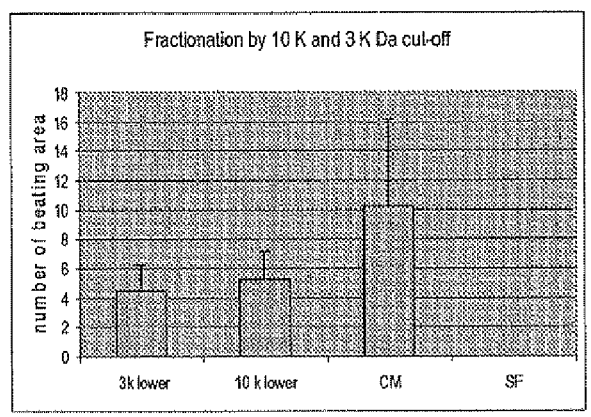
FIG. 2 shows the result of testing the flow-through fractions of END2-CM following size fractionation.
Figure 2:
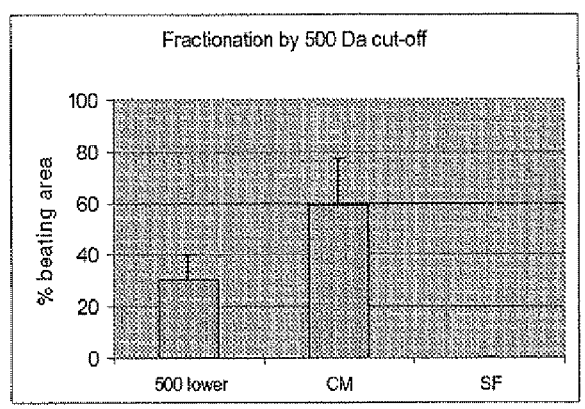
Figure 2:
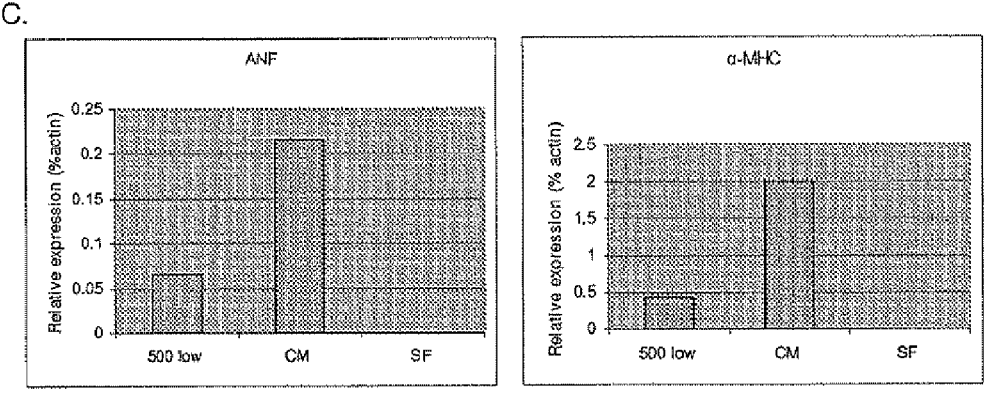

IV. Definition of a Mw Size Fraction of END2 Conditioned Media (END2-CM) Containing Cardiac-Inducing Activity The molecular range of the inducing factor(s) was determined by using Milipore Centricon concentrators to fractionate soluble molecules on the basis of molecular weight (Mw). Initially columns with molecular weight cut-offs at 30 k Da were used to examine if the activity could be separated by a high molecular weight cut-off. It was found that the activity was reproducibly present in the pass-through fraction (data not shown). Accordingly a 10 k Da and a 3 k Da column were used to fractionate the END2-CM, which at this cut off presumably removed all the proteins in the CM. The collected fractions were examined for their bioactivity by scoring the number of beating EBs at day 12 of the EB culture. As shown in FIG. 2, the END2-CM in the lower-phase of 3 k Da column exhibited a degree (35%) of induction activity, although it is not as high as that in the control END2-CM (62%). This suggested that the removal of proteins from the END2-CM caused a decrease of bioactivity but has not completely removed the activity. In order to further investigate if there is any activity in the small molecular fraction of END2-CM, the Amicon Stirred Cells system was adopted coupled with a Milipore ultrafiltration membrane which can fractionate samples at 500 Da cut-off. The device was pressurized by nitrogen gas to force fluid through the membrane while retaining the macromolecules with molecular size more than 500 Da. The pass-through was collected and tested to determine whether there was any activity contained in this fraction. As shown in FIG. 2B, 20%-40% beating areas were still found in the 500 Da lower-phase of the END2-CM when used to culture EBs. Quantitative RT-PCR of cells harvested at day 12 for two genes expressed in developing cardiomyocytes also confirm that these genes are expressed in hES cells exposed to the flow through fraction (FIG. 2C). Using either a 10 k Da and 3 k Da cut-off or after 500 Da cut-off the END2-CM bioactivity, although reduced, is still detectable in the flow through of all three columns suggesting that it is of a small molecular weight (Mw).

Figure 3:
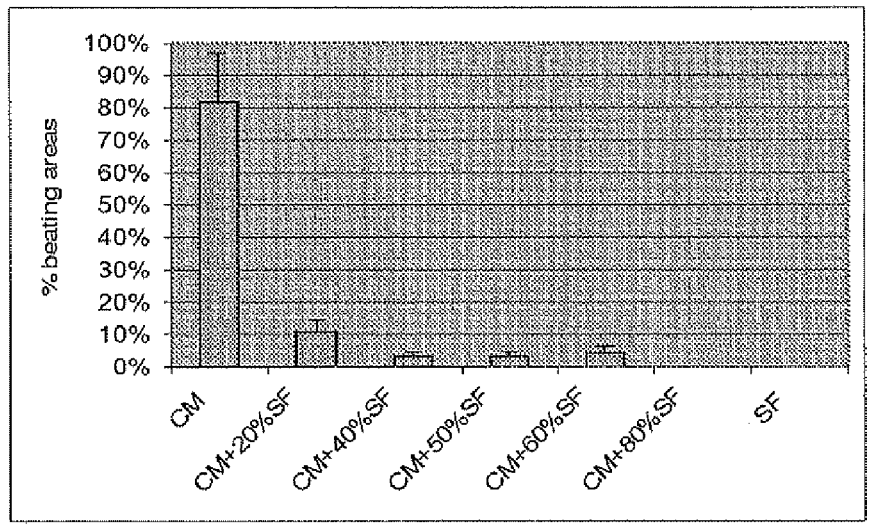
FIG. 3 shows the effect of dilution of END2-CM with SF medium.
Figure 3:
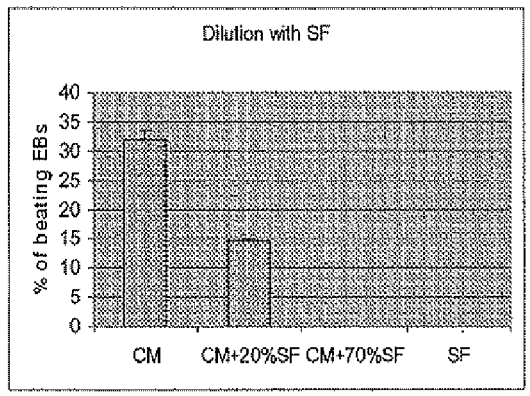
Figure 3:
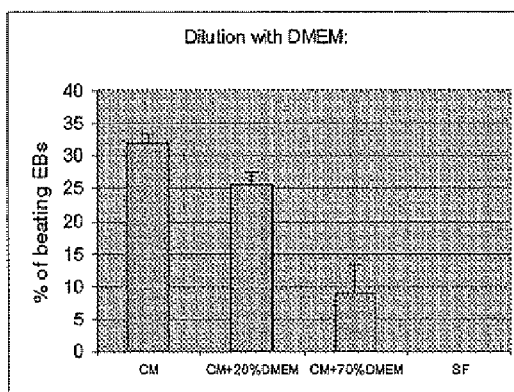

VI. Insulin in the SF Medium Inhibits hES Cell Cardiac Differentiation and is Depleted by END2 Cells During Conditioning To investigate whether END2-CM induction activity is dosage-dependent, END2-CM was diluted with SF media. END2-CM was serially diluted by addition of 20%, 40%, 50%, 60% and 80% of SF into the END2-CM. The results showed the bioactivity decreased significantly when 20% SF was added into END2-CM (equivalent to 80% END2-CM), and continued to drop to no activity detected when 20% SF was added into END2-CM (equivalent to 20% END2-CM) (FIG. 3). The high sensitivity of END2-CM to SF dilution suggested there might be inhibitory factor(s) from the SF medium.

The dilution by DMEM only without adding the rest of the 5 components was examined to determine whether it would give any difference compared to dilution by SF (equivalent to DMEM+5 components). A serial dilution of END2-CM by addition of 20%, 40%, 50%, 60% and 80% of SF medium and the number of beating areas scored at day 12 of EB culturing (FIG. 3A). A significant inhibition of END2-CM activity was observed with even low dilutions of the END2-CM by SF medium suggesting the presence of an inhibitor in the SF medium. Comparison of SF medium and DMEM medium shows that the inhibition of END2-CM is more pronounced in SF medium than would be expected by the simple dilution of the END2-CM (FIG. 3B).

As shown in FIG. 3B, the activity dramatically decreased in 20% SF media whereas 20% DMEM dilution was not as dramatic as occurred when SF medium was used for dilution. In 70% SF medium dilution of the END2-CM the activity was completely inhibited whereas there was still 9% average beating in 70% DMEM dilution. The result suggested that it is not DMEM but the S components (ITS, beta-mercaptoethanol, non-essential amino acid, L-glutamine, and antibiotics) in the SF medium that is contributing to the inhibitory effect. Among the 5 components, the most potential factors were likely to be insulin, transferrin and selenium contained in ITS, or beta-mercaptoethanol.

Figure 4:
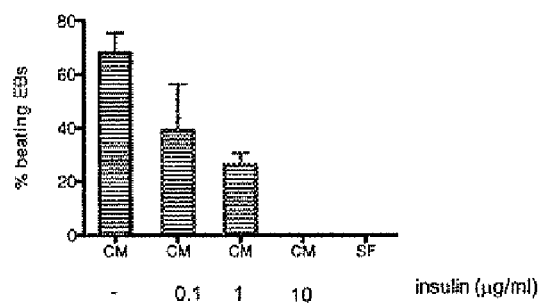
FIG. 4 show supplementation of insulin (0.1-10 ug/ml) into END2-CM completely abrogated cardiomyocyte's bioactivity.
Figure 4:
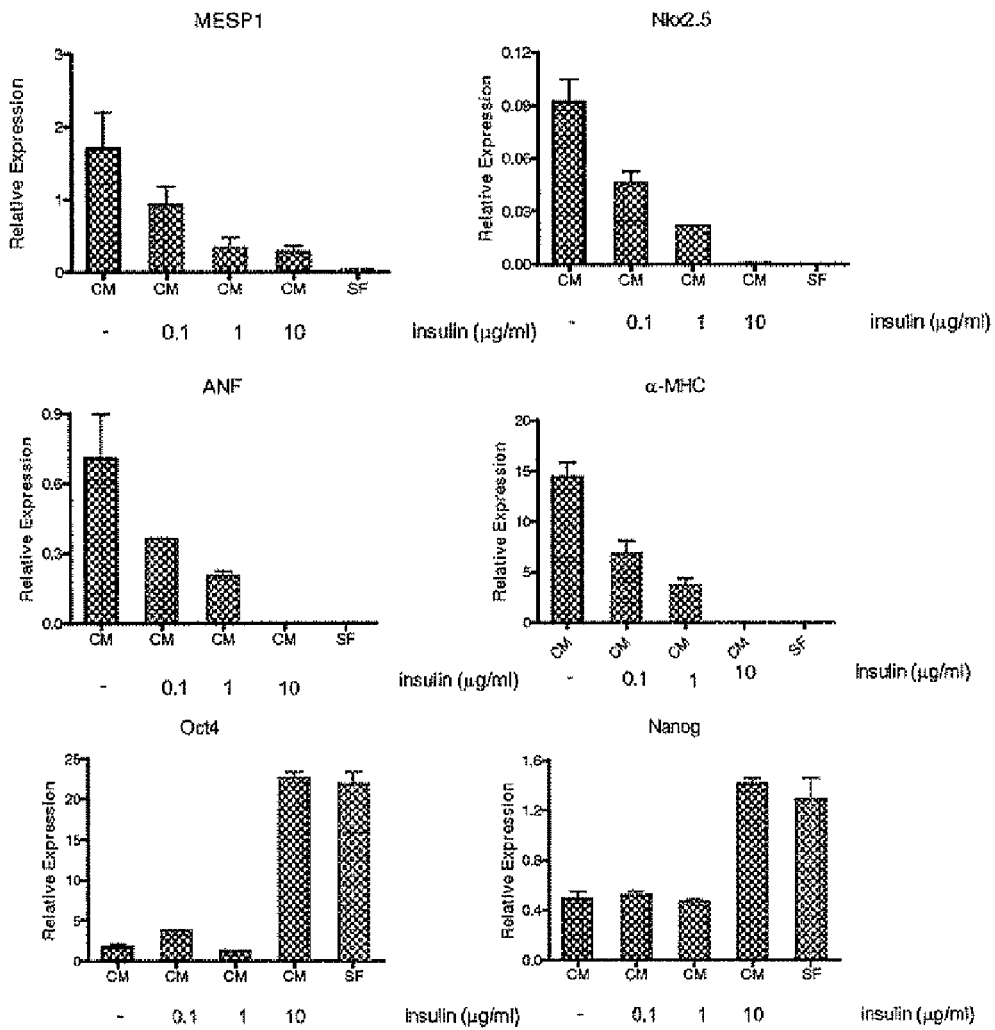

The components in the SF medium that contribute to the significant reduction effects were next investigated. Dilution experiments following the procedures described above by dilution of END2-CM using different combinations of DMEM with individual medium supplements were used (for example, DMEM plus β-mercaptoethanol, DMEM plus transferrin, DMEM plus insulin). The results indicated that the bioactivity decreased only when insulin was added into CM for dilution (data not shown). An alternative approach was taken in order to further demonstrate that insulin caused inhibitory effects. Insulin was spiked into the CM to check whether it could inhibit bioactivity in the CM in a manner similar to adding SF medium to CM as observed in FIG. 4A. The addition of insulin (0.1-10 µg/ml) to END2-CM resulted in a dose dependent inhibition of cardiomyocyte formation from hESC with a complete inhibition at the highest concentration of 10 µg/ml, an equivalent concentration to the insulin concentration in SF medium. The relative expression profile of early cardiomyocyte markers (MesP1, NRx2.5, ANF and α-MHC) also showed a dose dependent decrease in expression whereas two makers of pluripotent hESCs retained higher expression at the highest concentration of insulin (FIG. 4B).

This data strongly demonstrates that insulin concentration contributes to the inhibitory effects of SF medium when added to END2-CM.

Figure 5:
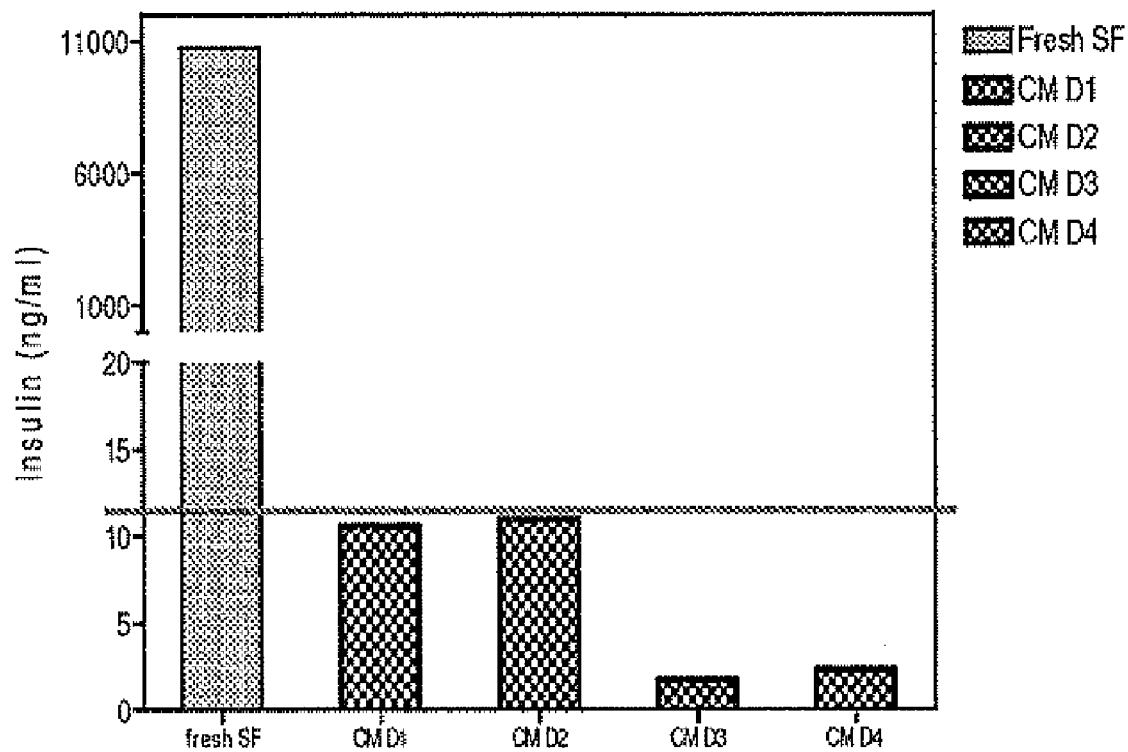
FIG. 5 shows an ELISA assay of insulin concentration in the SF medium used for conditioning over time.

The data above demonstrates that insulin has a negative impact on the END2-CM activity. In the preparation of the SF media, ITS is routinely added to the medium and contains high final levels of insulin (10 ug/ml). Without being limited by theory, it is postulated that the conditioning process by END2 cells could potentially reduce insulin contents in the SF medium. To address this question, the insulin concentration in the SF was analysed and compared with the insulin levels after different periods of conditioning in culture with END2 cells to generate END2-CM. The time-course of collecting END2-CM was at day1, day2, day3, and day4. An ELISA assay of insulin concentration in the SF medium used for conditioning over time (FIG. 5). The concentration of insulin in the SF medium, when exposed to END2 cells over a 4 day period decreases dramatically by almost a thousand fold by day 4, the time when END2-CM is used for hES cell differentiation to cardiomyocytes.

As the results show in FIG. 5, the insulin concentration in SF medium is 10.731 ug/ml (close to 10 ug/ml theoretical value in medium), whereas in END2-CM, it is within the range of 2-10 ng/ml for day 4 to day 1 CM, which is 1000 times lower than that in SF medium. This result demonstrates that the Insulin content in END2-CM is dramatically reduced by the END2 cells during the conditioning process.

Figure 6:
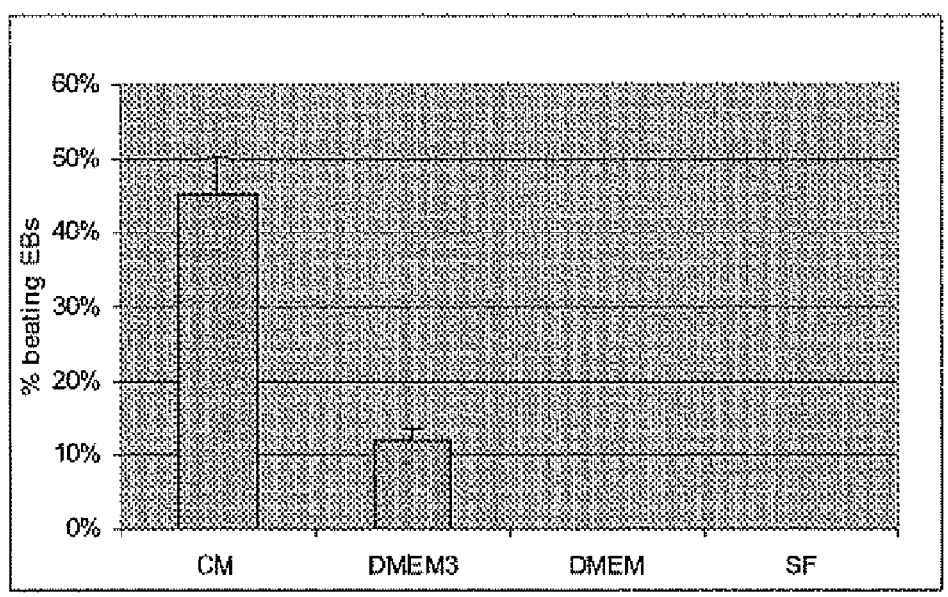
FIG. 6 shows that removal of insulin from the SF medium is permissive for hES cardiac induction.

VII. A Permissive Medium for Basic Cardiac Differentiation in the Absence of Insulin The SF medium is routinely used as a negative control in the hES cell cardiac differentiation system. This always gives no emergence of beating in the EBs grown in the SF medium suggesting that the SF media conditions are not permissive or inhibitory for cardiomyocyte formation. The ELISA assay showed that the insulin concentration in the SF medium is 1000 fold higher than levels in the END2-CM. Accordingly, removal of insulin from the SF medium which was not conditioned by END2 cells was tested for its sufficiency for cardiac induction. These media formulations consist of DMEM3 (DMEM, NEAA and β-mercaptoethanol) or DMEM (DMEM media alone with no supplements). Cardiac induction was examined in EBs cultured in DMEM3 or DMEM only. As the results show in FIG. 6, the removal of insulin from the SF medium is now permissive for hES cell cardiac induction. The result shows that DMEM3 medium now provides a permissive culture environment for hES cells to form cardiomyocytes although this is still lower than observed with END2-CM.

No beating was observed in DMEM only, possibly because the cells in the DMEM were in unfavourable growing conditions as there were no essential amino acids in the medium. Many EBs were observed to shedding cells in the DMEM culture and there was a high level of cell death.

VIII. Summary

The data in this example revealed that insulin in the SF medium strongly inhibited cardiac differentiation of hES cells. Insulin-ELISA assay showed insulin content was more than 1000 times lower in END2 CM as compared to SF, suggesting that insulin was depleted during the END2 conditioning. Taken together, the data indicate a dual role of END2 cells during the medium conditioning process, including removal of inhibitors by a depletion of inhibitory, factors like insulin (or possible other inhibitory substances), and release of inducing factor(s). Based on this discovery, a defined medium (DMEM3) for basic cardiac differentiation by removing the inhibitor (i.e. insulin) from the SF medium was developed. This insulin-free permissive medium will facilitate further discovery of factors which are involved in induction or enhancement of hES cell cardiac differentiation. The data also demonstrate that the END2-CM activity is likely due to both protein-based and non-protein low Mw factors.

Example 2

Microarray Data Analysis to Identify Cardiomyocyte Inducing Factors Produced by END2 Cells I. Materials and Methods
(i) Microarray Analysis The Microarray experiments were conducted using Agilent Mouse 20k Developmental Oligo array or genome 40k Oligo array technology. MES-1 was used as a reference cell line as it derived from the same parental cell p19 EC cell line as END2 but negative in its induction of cardiac differentiation. Two replica array datasets with dye swap were generated in two independent array experiments. Only features' expression calls were positive and significant above background assigned by the "Agilent G2565AA Feature Extraction Software" were accepted for analysis. The array data files were imported into GeneSpring 7.1 (Silicon Genetics) for data analysis. The expression ratios (Cy5/Cy3: ratio of the median) were calculated and transformed to log 2. Log 2 expression ratios were then normalized by intensity-dependent LOWESS normalization. The differential expressed genes were identified as those showing significant differential expression (p<0.01). Gene RefSeqIDs, UnigeneClusterID, gene name and symbols are adopted from Unigene build #142.

(ii) PGI2 ELISA Assay

END2 and MES1 conditioned media were collected at day 1, 2, 3 and 4. Measurement of prostaglandin I2 (PGI2) concentration in CM medium was determined in duplicates using commercial enzyme immunoassay kit—6 keto Prostaglandin F1α EIA (6 keto PGF1α) kit (Cayman Chemical Co, USA, cat#515211). The assay was performed according to the manual's instruction, DMEM was used as blank and dilution solution for standards preparation. The assay results were calculated based on the standard curve generated in parallel and using a spreadsheet program provided by Cayman website (www.caymanchem.com/analysis).

(iii) Preparation of Growth Factors

The recombinant human Bmp6 (R&D), Fgf9 (CytoLab), Scf (CytoLab), and Igf2 (R&D) were reconstituted as stock solution in accordance with instructions provided by suppliers. The GFs were added into CM at final 10 ng/ml before culturing and during each medium changes.

II. Microarray Data Analysis to Identify Secreted Factors in END2 Cells

In order to identify potential factors that may be responsible for END2-CM cardiomyocyte inducing activity, genes expressed in END2 cells or differentially expressed between END2 and MES1 cells were examined. MES-1 was used as a reference as it derived from the same parental cell p19 EC cell line as END2 but negative in its induction of cardiac differentiation. 994 outlier genes differentially expressed between END2 and MES1 were extracted and 453 genes were extracted showing at least 2 fold up-regulation in END2 cell compared to MES-1 (data not shown).

III. Identification of PGI2 as a Component of END2 CM

Among this gene expression data set the extraordinarily high level of expression of two key synthase enzymes which are involved in Prostaglandin I2 (PGI2) synthesis was noted. The transcript expression level of Ptgis and Ptgs1 (Cox1) were 100 fold, 9.9 fold respectively in END2 cells in comparison with MES1 cells (Ptgis Genbank accession number: AK0036723; Ptgs1 (Cox1) Genbank accession number: BC005573). PGI2 is derived from arachidonic acid and produced by the cyclooxygenase (COX) system. Arachidonic acid, is first converted to PGH2 by prostaglandin-endoperoxide synthase (Ptgs or Cox1), and PGH2 is subsequently converted to PGI2 by the action of prostacyclin synthase (Ptgis).

Figure 7:
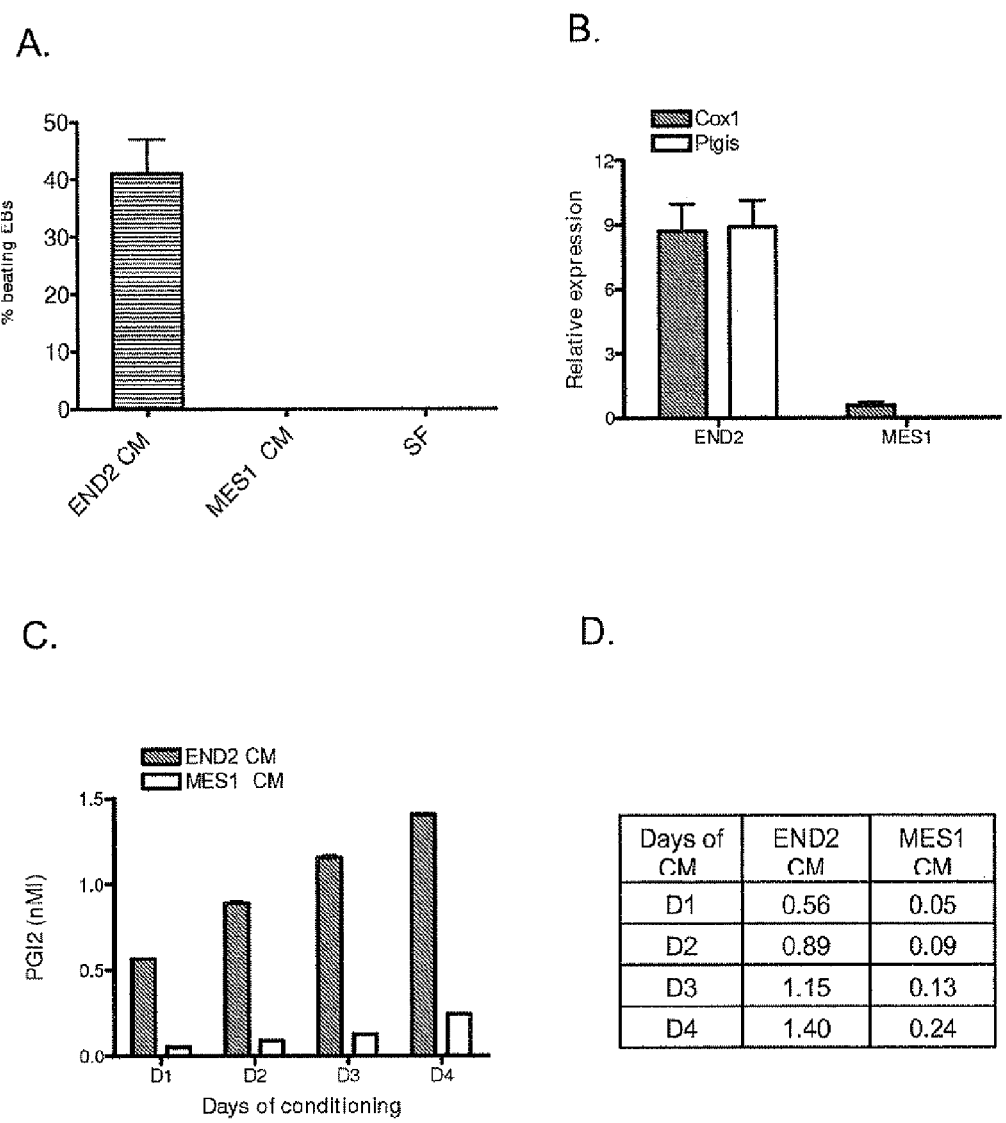
FIG. 7 shows an estimation of PGI2 levels in the END2 condition media.

To further determine whether the END2-CM contained detectable levels of PGI2 we analysed the concentration of a PGI2 stable metabolite (6 keto PGF1α) produced by the END2 and the MES1 cell lines by ELISA assay (FIG. 7). The cardiomyocyte inducing activity of END2-CM was compared with a control cell line MES1, also derived from the same embryonic carcinoma cell line, P19. Only END2-CM induced hES cells to form beating cardiomyocytes when they formed EBs (FIG. 7A). As comparative microarray data indicated higher relative expression of two enzymes involved in the synthesis of the PGI2 Cox1 (Ptgs1) and Ptgis, their relative expression levels were further examined by RT-PCR and their expression were 10- to 100-fold higher respectively between the END2 cell line and the non-inducing MES1 cell line (FIG. 7B).

Conditioned medium from END2 cells or MES1 cells were also collected after day 1, 2, 3 and 4 of conditioning and the potential PGI2 concentrations were indicated by the presence of its stable metabolite, 6-keto $PGF_{1\alpha}$ detected by the ELISA assay (FIG. 7C.) Differences in the concentration of a stable PGI2 metabolite, 6-keto $PGF_{1\alpha}$ in END2-CM vs. MES1-CM were apparent and higher concentrations of $PGF_{1\alpha}$ accumulated in END2-GM compared to the MES1-CM. The concentrations in END2-CM from day 1 to day 4, were within the range of 0.5 nM to 1.5 nM, whereas the concentration in MES1-CM from day 1 to day 4 were within the range of 0.05 to 0.25 nM (FIG. 7D). There is also an approximate 0.3 nM increase in concentration each day in END2-CM compared to an approximate 0.03 increase each day in MES1-CM such that by day4 the accumulated PGI2 produced by END2 cells was approximately 6 fold higher when compared to MES1 (FIG. 7D). These results indicate that the up-regulation of Ptgs1 (Cox1) and Ptgis resulted an elevated level of PGI2 production in END2 cells and its presence in the END2-CM compared to the MES1 cell line.

IV. Quantitative RT-PCR Validated the Expression of the Selected Candidate Protein Factors A subset of 116 genes encoding soluble and secreted protein factors in END2 cells were also identified by mircroarray analysis to END2 gene expression (Table 1). As the activity of the END2-CM could also be reduced by protein denaturants (Example 1) these represent candidate genes potentially associated with secreted proteins present in the conditioned media. This subset of genes identified growth factors and ligands involved in Bmp, Fgf, Wnt, and Igf gene families that have previously been demonstrated to be involved in mouse cardiac differentiation. Several of these growth factors were evaluated to determine their effects in hES cell cardiomyocyte induction.

Figure 8:
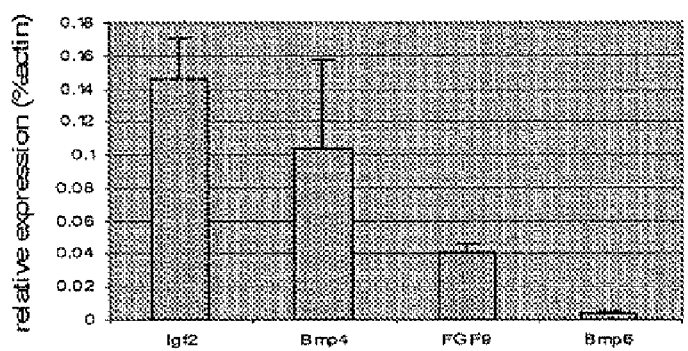
FIG. 8 shows that an addition of growth factors family members Fgf9, Bmp6, Scf or, Igf2 could enhance CM induction activity when added to END2-CM.
Figure 8:
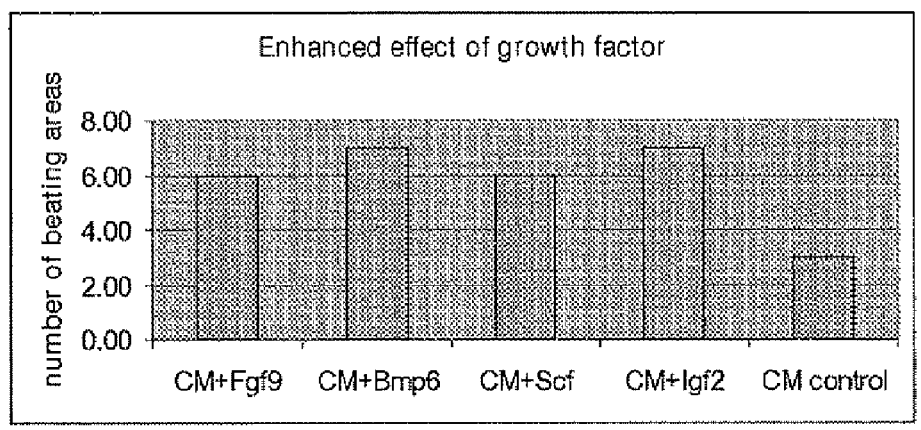

V. Enhanced Effects of Fgf9, Bmp6, Bmp4, Scf, and Igf2 on Induction of Cardiac Differentiation from hES Cells Microarray gene expression analysis on END2 cells has identified Fgf9, Bmp6, Scf (stem cell factor), and Igf2 as secreted factors produced by END (Table 1). In order to verify the fidelity of the data generated from the microarray data these genes were selected and their expression by END2 cells was validated by quantitative RT-PCR (FIG. 5A). The expression of Bmp6, Fgf9, Bmp4 and Igf2 genes was detected by RT-PCR and the level of expression generally correlated with the signal intensity obtained from microarray gene expression analysis (data not shown). Four of these growth factors identified were also tested at a final concentration of 10 ng/ml in the END2-CM and the number of beating areas were scored at day 12 of culture and approximately 10-25 total EBs within one well of 6-well dish were counted. The results of these experiments indicate that the addition of growth factors of the FGF, BMP, SCF and IGF family members could enhance the END2-CM cardiomyocyte induction activity when supplemented to END2-CM and increased the number of beating areas compared to END2-CM alone (FIG. 8B).

VI. Summary

Microarray analysis used to obtain an expression profile of genes expressed by the END2 cell line as well as genes that may be increased in their expression between the END2 cell line and a control MES1 cell line. This analysis revealed that a potential small molecule, PGI2 was likely produced at higher levels by END2 cells compared to MES1 cells. This was confirmed by an analysis of the END2 conditioned media for PGI2 concentration. The possibility that a small non protein molecule was responsible for part of the END2-CM bioactivity is also supported by the effects of protein denaturants and molecular weight fractionation in Example 1.

Further analysis of genes that are expressed by END2 that encode for potentially secreted protein growth factors also revealed several members of the growth factor families including the FGF, BMP and IGF families. When recombinant proteins of these families were supplemented to the END2-CM an enhanced cardiomyocyte activity of the END2-CM was observed.

Example 3

Prostaglandin I$_2$ (PGI2) is an Active Component of END2 CM and Able to Increase hES Cell Cardiac Differentiation I. Materials and Methods
(i) Medium Supplementation with PGI2
Prostaglandin I$_2$ or PGI2-Na {(5Z,9α,11α,13E,15S)-6,9-Epoxy-11,15-dihydroxyprosta-5,13-dien-1-oic acid Sodium salt] was obtained from Sigma-Alorich. It was dissolved in 90% Ethanol at 2 mM as stock solution and then diluted with PBS before adding to bSFS at final concentration of 0.2 uM, and 2 uM. Medium change with addition of respective amounts of PGI2 was performed at day 3, 6 and 9 after EB formation.
II. Results
Factors found in the END2 conditioned media (CM) and involved in the ability of END2 cells to induce hES cell cardiac differentiation were identified. Accumulated data from studies on CM (physiochemical properties and size fractionation) from the previous examples suggested that the inducing factor in END2-CM is potentially a small molecule that is not a protein. Microarray analysis (Example 2) reveals one such potential candidate, Prostaglandin I$_2$ (PGI2).

Figure 9:
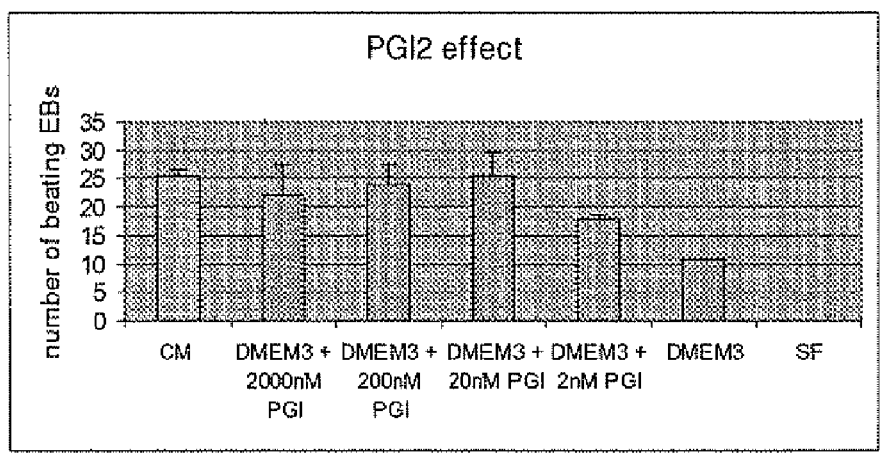
FIG. 9 shows that effective cardiac induction by Prostaglandin $I_2$ (PGI2) supplemented to DMEM3 gave levels of cardiomyocyte induction comparable to END2-CM.
Figure 9:
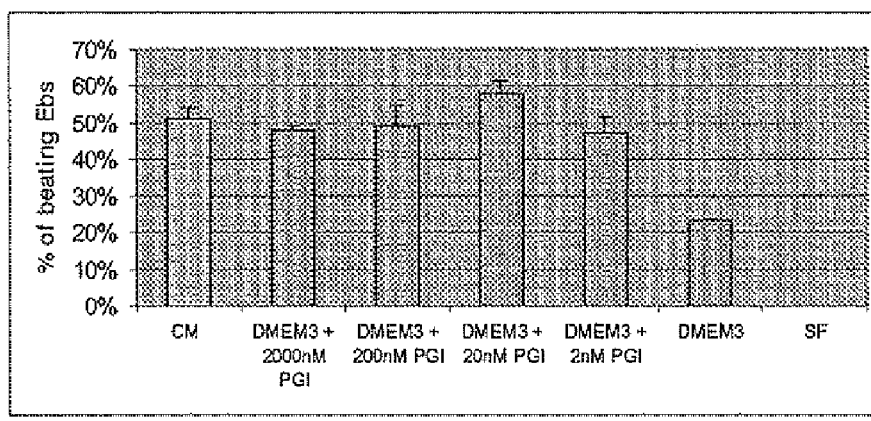

The potential of PGI2 to induce cardiomyogenic differentiation of hES cells was tested by adding PGI2 to unconditioned permissive basic media (DMEM3) at final concentrations of 2 nM, 20 nM, 200 nM, and 2000 nM and the number of beating EBs was scored at day 12 of culture. FIG. 9 shows that effective cardiac induction by Prostaglandin I$_2$ (PGI2) supplemented to DMEM3, an insulin free medium, could achieve levels of cardiomyocyte induction comparable to END2-CM and the number of beating EBs was similar in both END2-CM and DMEM3 supplemented with PGI2. As shown in FIG. 9, significant increases in the percentage of beating EBs was observed in the PGI2 supplemented media for all concentrations, with the highest number of beating EBs at 20 nM and 200 nM concentration range in comparison with basic DMEM3 medium. This result strongly suggested that PGI2 contributed to the cardiac inducing activity found in the END2-CM.

Prostaglandin I2 (Prostacyclin, PGI2) is involved in platelet aggregation, vasoconstriction, and reproductive functions. It is a potent vasodilator and anticoagulant. PGI2 acts on a G protein-coupled cell surface receptor called IP. Activation of IP by PGI2 leads to an increase in intracellular cAMP levels which in turn leads to phospholipase C activation and Ca$^{2+}$ mobilization. PGI2 signalling leads to a wide range of physiological effects in different tissues, however, it has not been associated with cardiomyocyte differentiation. Aside from its role in embryo implantation, there is no known direct role of PGI2 in embryonic development (Cha, 2005). A recent study suggests a novel signalling of PGI2 via nuclear receptors, peroxisomal proliferator-activated receptors (PPARs). PPARs belong to a family of ligand-activated transcription factors and heterodimerization with a retinoid X receptor is a prerequisite for their DNA binding activity and recruitment of transcriptional cofactors is required to activate target genes (Lim, 2005). However, PPARs signalling mechanisms are largely unknown, although it is indicated that they have emerged as a master transcriptional regulator of many aspects of physiological responses and metabolism whose activity can be modulated by direct binding of small molecules (Lehrke, 2005).

III. Summary
The discovery of PGI2 as the inducing factor in END2 CM is a critical one since the process of generating cardiomyocytes from hES cells can now be made using defined reagents and therefore under GMP (Good manufacturing Practice). Conditioned media from a mouse cell line is no longer required also removing the issues associated with using animal products. The present example provides defined conditions to induce cardiomyocytes which is both simple and cost-effective.

Figure 10:
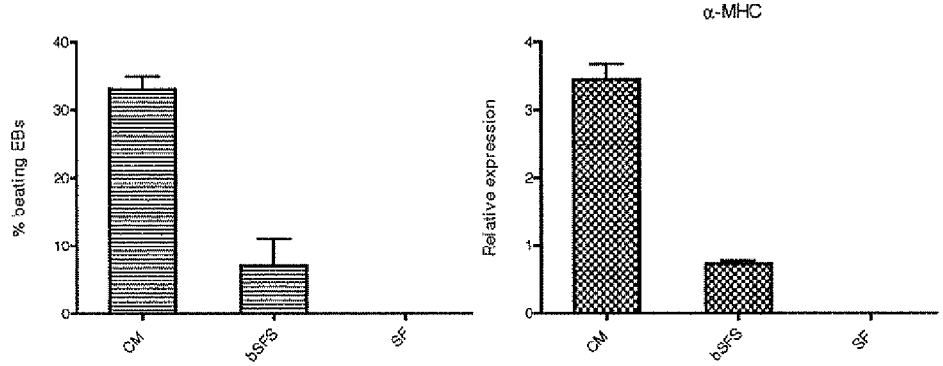
FIG. 10 shows the development of a defined serum free medium permissive for cardiomyocyte formation and robust cell growth.
Figure 10:
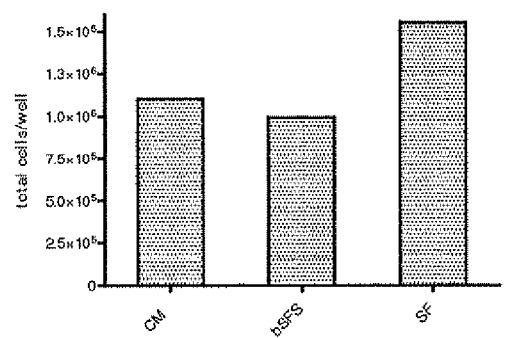
Figure 10:
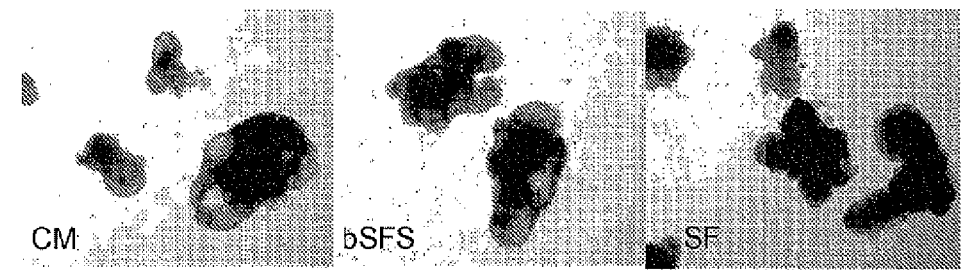

Example 4 bSFS Medium: Addition of Transferrin and Selenium to the Permissive Medium DMEM3 Increases Cell Viability but does not Inhibit hESC-Derived Cardiomyocyte Formation I. Material and Methods
bSFS medium consists of the SF medium but without added insulin (see Example 1)
II. Results
To further investigate the role of other media supplements of the SF medium beside insulin we used the permissive serum free media DMEM3 that does not contain insulin and supplemented it with Transferrin and Selenium. This media is termed bSFS media. The results show that both Transferrin and Selenium supplementation is not inhibitory and both are required for robust induction of cardiomyocytes and growth of hES cells in culture as EBs (FIG. 10).

A comparison of the effect of the bSFS medium with SF and END2-CM indicate that this more complete defined serum free media (bSFS) is still permissive for the formation of hESC-derived cardiomyocytes in a manner similar to DMEM3 and also expresses early cardiac markers (α-MHC) (FIG. 10A). Cell growth and viability in bSFS is also equivalent to that obtained with END2-CM and the beating EBs formed are comparable with those formed in END2-CM. A viable cell count analysis using Trypan blue revealed that the total cell number in bSFS medium was comparable to END2-CM (FIG. 10B) and the large amount of cell death observed in less complete serum free media (e.g DMEM or DMEM3) was also not apparent when EBs are grown in bSFS and were similar to EBs grown in either END2-CM or SF medium that contain insulin (FIG. 10C).

III. Summary
Addition of Transferrin and Selenium to the permissive serum free media DMEM3, indicate that Transferrin and Selenium are essential media components that can significantly improve cell growth. These supplements at the concentrations tested also do not impact on the permissiveness of this more complete serum free media to form cardiomyocytes from hES cells.

Example 5

Supplementation of bSFS+PGI2 with Another Small Molecule SB203580 Further Increases the Efficiency Cardiomyocyte Formation I. Materials and Methods
(i) Addition of PGI2 and SB203580 PGI2
Prostaglandin I$_2$ or PGI2-Na {(5Z,9α,11α,13E,15S)-6,9-Epoxy-11,15-dihydroxyprosta-5,13-dien-1-oic acid Sodium salt] was obtained from Sigma-Aldrich. It was dissolved in 90% Ethanol at 2 mM as a stock solution and then diluted with PBS before adding to the differentiation medium bSFS at a final concentration of 2 uM. p38 MAPK inhibitor SB203580 or [4-(4-Fluorophenyl)-2-(4-methylsulfinylphenyl)-5-(4-pyridyl)1H-imidazole] (Calbiochem) was dissolved in DMSO (13 mM stock solution) and added to bSFS at a final concentration of 5 uM. Medium changes were performed on days 0, 3, 6 and 9 after EB formation, and fresh PGI2 and/or SB203580 was added with each medium change.

(ii) Cardiomyocyte Quantification via Cytospin

EBs were washed twice with PBS (without calcium and magnesium) and dissociated to single cells using trypsin (Invitrogen). Cells were collected via centrifugation at 2500 rpm for 4 min at RT. The cell pellet was resuspended in PBS and a cell count performed. 100,000 cells were spun at 500 rpm for 5 min onto glass slides at low acceleration using a cytospin system (Shandon). Adherent cells were fixed, stained and the total cell number (DAPI staining of cell nuclei) and the number of sarcomeric alpha myosin heavy chain positive cells (αMHC, MF-20 Ab, Hybridoma Bank, Iowa; 1:200 followed by respective rabbit-anti mouse Cy3-labeled secondary Ab 1:500, Zymed) were counted in at least 3 independent fields of view at 20× magnification with at least 300 nuclei per field; fields were randomly selected in the DAPI channel (Zeiss Axiovert 200M, Zeiss) avoiding bias towards cardiomyocyte content. The percentage of cardiomyocytes compared to the total cell nuclei number was calculated.

Figure 11:
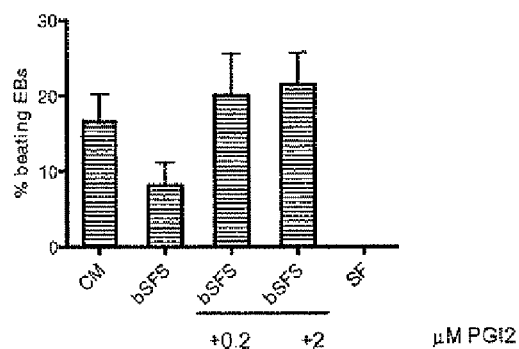
FIG. 11 shows the defined serum free media bSFS supplemented with PGI2 has equivalent cardiomyocyte inducing activity to END2-CM.
Figure 11:
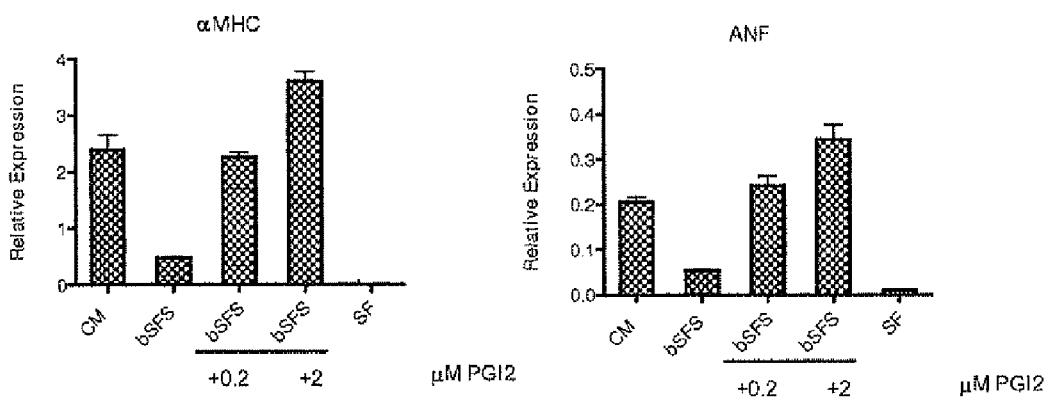
Figure 11:
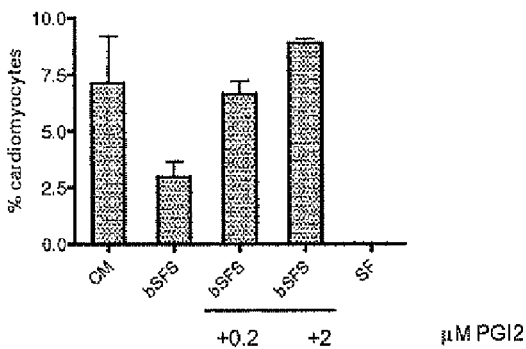
Figure 12:
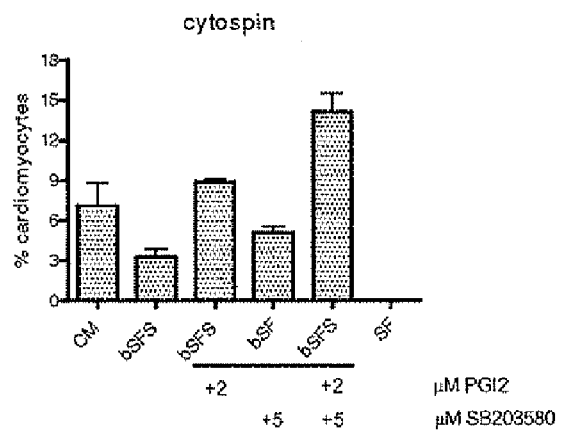
FIG. 12 shows supplementation of bSFS+PGI2 medium with the compound SB203580 further increases the efficiency of cardiomyocyte formation.
Figure 12:
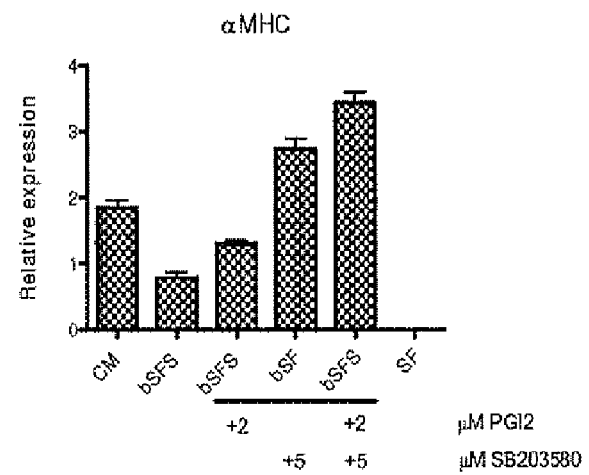
Figure 12:
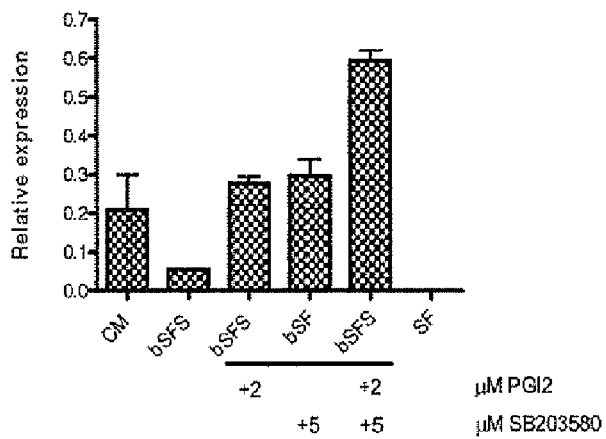

II. Analysis of the Effect of the Small Molecules PGI2 and SB203580 Added to the bSFS Medium on hES Cell Cardiomyocyte Formation A fully defined serum free medium described in Example 4 termed bSFS (DMEM, L-glutamine, Non-Essential Amino Acids, Transferrin, Selenium and Penicillin/Streptomycin) was used a the permissive serum free medium to test the effects of the small molecules PGI2 and SB203580 on cardiomyocyte formation from hESC (FIG. 11 and FIG. 12). Addition of PGI2 to the bSFS medium at concentrations of 0.2 and 2.0 μM resulted in an increase in cardiomyocyte inducing activity to levels similar to that observed with END2-CM (FIG. 11A) and the expression of two cardiomyocyte marker genes α-MHC and ANF showing equivalent, if not enhanced expression in bSFS+ PGI2 medium compared to END-CM (FIG. 11B). Furthermore, quantification of cardiomyocyte cell number by cytospin and using MF20 immunohistochemistry also showed that the percentage of the overall cell population that forms cardiomyocytes is also equivalent to that observed in END2-CM cultures (FIG. 11C).

We next investigated the effect of another small molecule, SB203580 an inhibitor of the p38 MAPK signalling pathway supplemented to bSFS medium. hES cell differentiation was performed in EBs in suspension for 12 days before the percentage of cardiomyocytes and the relative expression of cardiac α-MHC and ANF expression was analysed by cytospin or Q-PCR. Supplementation of bSFS or bSFS+PGI2 medium with the compound SB203580 (2 uM of PGI2 and/or 5 uM of SB203580) further increases the efficiency of cardiomyocyte formation compared to bSFS alone or bSFS+PGI2. The results clearly indicate that the addition of 2 uM PGI2 and 5 uM SB203580 in combination resulted in an enhanced induction of cardiomyocyte formation. A 2 to 3-fold higher percentage of cardiomyocytes was present in this medium at day 12 compared to END2-CM alone and increases of upto 5 fold occurred when compared with bSFS alone (FIG. 12A). Analysis of the cardiac marker gene expression of α-MHC and ANF also indicated an elevated expression in the bSFS medium supplemented with PGI2 and SB203580 in combination (FIGS. 12 B and C). This clearly demonstrates that the fully defined serum free medium bSFS+2 uM PGI2+5 uM SB203580 is more efficient than either END2-CM alone or bSFS medium supplemented with PGI2 or SB203580 separately.

III. Summary

By using a defined serum free media bSFS in combination with a compound identified as being present in the END2-CM, PGI2 and another small molecule SB203580 the efficiency of hES cell cardiomyocyte production has been increased. The level achieved in this fully defined medium (bSFS+2 uM PGI2+5 uM SB203580) was much higher than that observed in the END2 CM and as such represent a potentially useful and GMP-grade media useful for the production of clinically compliant hES cell-derived cardiomyocytes.

Example 6

Embryoid Body (EB) Formation and hESC Differentiation into Cardiomyocytes in Fully Defined Media (SF, KO-SR, bSFS) in a Scalable Spinner Flask Process I. Material and Methods For hES cell culture on human feeder cells, see Example 1.

(i) Culture Media:

Defined basic serum free medium (bSFS): DMEM supplemented with 1× MEM non-essential amino acids (Invitrogen), 2 mM L-Glutamine (Invitrogen), 0.0055 mg/ml Transferrin (Roche), 5 ng/ml sodium Selenite (Sigma), 0.1 mM β-mercaptoethanol, with or without Penicillin/Streptomycin (Invitrogen).

KO medium: KO-DMEM with 20% KOSR in 0.1 mM β-mercaptoethanol, 1% MEM non-essential amino acids, 2 mM L-glutamine, FGF2 (10 ng/ml) with or without antibiotics (Penicillin/Streptomycin; all reagents from Invitrogen).

SF medium: DMEM supplemented with MEM 1× non-essential amino acids, 2 mM L-Glutamine, 1× Insulin-Transferrin-Selenium, 0.1 mM β-mercaptoethanol with or without Penicillin/Streptomycin (all reagents from Invitrogen). The medium was used to generate END2-CM or directly for hES differentiation.

II. Addition of the p38 MAP Kinase Inhibitor SB203580 p38 MAPK inhibitor SB203580 or [4-(4-Fluorophenyl)-2-(4-methylsulfinylphenyl)-5-(4-pyridyl)1H-imidazole] (Calbiochem) was dissolved in DMSO (13 mM stock solution) and added directly to bSFS or another respective medium at a final concentration indicated in the examples and figures.

III. Cardiomyocyte Quantification via Cytospin

This was determined as in example 5.

IV. Results

To induce hESC cardiac differentiation in a scalable suspension culture process hESC were grown on human feeder cells for 7 days, washed with PBS and incubated with the Collagenase NB6 (Serva, 2.5 mg/ml in PBS) for 35 min to harvest the cells from 10 cm cell culture dishes. hESC from 5×10 cm dishes were collected in a 50 ml disposable tube (Falcon), washed twice with either 25 ml of SF or KO medium respectively, suspended in 50 ml of either SF or KO medium and transferred into a 100 ml spinner flask with a bulb-shaped stirring device (Integra Biosciences). Stirring at 50 revolutions per minute (50 rpm) was performed during the whole experiment. After overnight incubation SF or KO medium was replaced by bSFS medium with a final concentration of 5 μM SB203580. Before adding bSFS cells were collected by gravity at the bottom of the flask and washed twice with DMEM (Invitrogen). 30 ml of the culture medium was replenished by fresh bSFS+SB203580 (to generate a 5 µM final concentration in 50 ml) every 3 days. At day 12 the percentage of beating EBs (relative to the total EB number) was assessed followed by EB dissociation into single cells to determine the total cell number as well as the percentage of cardiomyocytes via cytospin.

EB formation overnight in SF medium followed by addition of bSFS+5 µM for 12 days resulted in 57.62% beating EBs (87 beating EBs in a spinner flask-derived aliquot of 151 EBs in total), a total cell yield of $4.96 \times 10^7$ cells per spinner flask (in the 5 ml medium volume in one spinner flask) and a proportion of 15.14% cardiomyocytes. This resulted in a yield of $7.51 \times 10^6$ cardiomyocyte per spinner flask.

EB formation overnight in KO medium followed by addition of bSFS+5 µM for 12 days resulted in 92.63% beating EBs (88 beating EBs in a spinner flask-derived aliquot of 95 EBs in total), a total cell yield of $5.09 \times 10^7$ cells per spinner flask (in the total 50 ml medium volume in one spinner flask) and a proportion of 19.1% cardiomyocytes. This resulted in a yield of $9.72 \times 10^6$ cardiomyocyte per spinner flask.

V. Summary

These results demonstrate that hESC differentiation into cardiomyocytes can efficiently be induced by the direct inoculation of hESC into scalable suspension culture systems in chemically defined media such as SF, KO, and bSFS. The cardiomyocyte differentiation is particularly efficient in bSFS (a medium that was defined based on experiments utilizing END2-cell conditioned medium termed END2-CM) in conjunction with SB203580 at a 5 µM concentration. Utilizing this example, those skilled in the art will be able to use other media and culture systems for EB formation and hESC differentiation in large scale.

Example 7

Stimulation of Cardiac Differentiation and Cell Proliferation by Addition of SB203580, Recombinant Growth Factor Analogue of Human Insulin-Like Growth Factor I (L-IGF-I), Acetic Acid (AA), and/or Basic Fibroblast Growth Factor (FGF2) into bSFS or END2-CM Medium I. Material and Methods
(i) For hES culture on human feeder cells, see Example 1. For bSFS and SF medium see Example 5 and 1. For embryoid body (EB) formation see example 1. For the preparation of END2 conditioned medium (END2-CM) see example 1. For Cardiomyocyte quantification via Cytospin, see Example 5.
(ii) Addition of the p38 MAP Kinase Inhibitor SB203580 p38 MAPK inhibitor SB203580 or [4-(4-Fluorophenyl)-2-(4-methylsulfinylphenyl)-5-(4-pyridyl)1H-imidazole] (Calbiochem) was dissolved in DMSO to form a 5 mM or 13 mM stock solution respectively and added directly to bSFS or another respective medium at a final concentration indicated in the examples and figures.
(iii) Addition of L-IGF-I (LONG R3 IGF-I; a Recombinant Growth Factor Analogue of Human Insulin-Like Growth Factor I; SAFC Biosciences)

L-IGF-I was dissolved in 100 mM acetic acid to obtain a stock of 1 mg/ml A working stock solution of 5 µg/ml L-IGF-I was then diluted from the 1 mg/ml stock, and added directly to bSFS or another respective medium at a final concentration indicated in the examples and figures.
(iv) Addition of FGF2 (Basic Fibroblast Growth Factor; Invitrogen)

FGF2 was dissolved in 1×PBS, and a 10 mg/ml of stock solution was obtained. It was added directly to bSFS or another respective medium at a final concentration indicated in the examples and figures.
(v) Addition of AA (Acetic Acid; Sigma)

A stock solution of 500 µM acetic acid was added directly to bSFS or another respective medium at a final concentration indicated in the examples and figures.

II. Results

In this experiment the effect of SB203580 (SB), Acetic Acid (AA) L-IGF-I, and FGF2 (when added alone or in combination into END2-CM or bSFS) on cardiac induction of differentiating hESC was investigated and compared to END2-CM or bSFS medium alone. hESC were differentiated as EBs in suspension culture in a 6-well plate format as described above. Readouts were performed on day 13. The percentage of beating EBs was counted, the average total cell number per well was counted via a cytometer after EBs dissociation with trypsin. The percentage of cardiomyocytes was counted via cytospin and the cardiomyocyte yield was calculated from the total cell count per well and the percentage of cardiomyocytes. Results are presented in Table 2 which provides an analysis on day 12 EBs differentiated in the presence of respective media added with substances as indicated in the table. Differentiation was performed in suspension in a low attachment 6-well format. Average numbers per well of a 6-well plate are presented.

TABLE 2

| Medium | % beating EBs | % Cardio-myocytes | Total cell count × $10^6$ | Cardio-myocyte yield × $10^5$ | Normalized Cardiomyocyte Yield |
|---|---|---|---|---|---|
| | | | | | normalized to END2-CM |
| END2-CM | 25.03 | 5.44 | 2.10 | 1.14 | 1 |
| END2-CM + 5 µM SB203580 | 56.28 | 5.51 | 3.63 | 2.00 | 1.75 |
| END2-CM + 5.0 ng/ml L-IGF-I | 18.61 | 2.84 | 1.94 | 0.55 | 0.48 |
| END2-CM + 25.0 ng/ml FGF2 | 22.46 | 3.88 | 1.83 | 0.71 | 0.62 |
| | | | | | normalized to bSFS |
| bSFS | 12.49 | 2.11 | 1.18 | 0.25 | 1 |
| bSFS + 5 µM SB203580 | 66.62 | 5.75 | 2.08 | 1.19 | 4.76 |
| bSFS + 5.0 ng/ml L-IGF-I | 8.92 | 4.18 | 1.13 | 0.47 | 1.88 |
| bSFS + 5 µM SB203580 + 5.0 ng/ml L-IGF-I | 37.09 | 13.79 | 1.75 | 2.41 | 9.64 |

TABLE 2-continued

| Medium | % beating EBs | % Cardio-myocytes | Total cell count × $10^6$ | Cardio-myocyte yield × $10^5$ | Normalized Cardiomyocyte Yield |
|---|---|---|---|---|---|
| bSFS + 5.0 µM AA | 15.60 | 3.31 | 1.03 | 0.34 | 1.35 |
| bSFS + 5 µM SB203580 + 5.0 µM AA | 35.97 | 10.01 | 3.38 | 3.38 | 13.52 |
| bSFS + 25.0 ng/ml FGF2 | 5.27 | 3.10 | 2.40 | 0.74 | 2.96 |
| bSFS + 25.0 ng/ml FGF2 + 5 µM SB203580 | 19.51 | 5.70 | 3.30 | 1.88 | 7.52 |

The key parameter that indicates the success of the hES cell differentiation process in this experiment is the cardiomyocyte yield which is calculated from the total cell number and the percentage of cardiomyocytes observed. As shown in Table 2 the addition of SB203580 at a 5 µM concentration resulted in a 1.75-fold increase of the cardiomyocyte yield in END2-CM and a 4.76-fold increase of the cardiomyocyte yield in bSFS. The addition of L-IGF-I at a 5.0 ng/ml concentration, AA at a 5.0 µM concentration, as well as FGF2 at a 25.0 ng/ml concentration into bSFS also resulted in some increase regarding the cardiomyocyte yield compared to bSFS alone. Furthermore a synergistic effect between these factors in combination with SB203580 at a 5 µM concentration in bSFS was observed.

III. Summary

This result indicates that factors identified in the previous examples can be applied, in combination to achieve efficient yields of cardiomyocytes.

Example 8

Generation of Transgenic hES Lines Carrying the α-MHC-neo Construct for Selection of the Cardiac Lineage I. Materials and Methods (i) Embryonic Stem Cell Culture and Transfection hES3 cells were cultured on mitotically-inactivated human fibroblasts CCD919 (ATCC). The hES medium is comprised of DMEM supplemented with 20% KOSR, 100 µM non-essential amino acids, 2 mM L-glutamine, 0.5% v/v penicillin/streptomycin, and 1×ITS (Invitrogen). For routine passaging hES3 cells were split by manually cutting the colonies and transferring them to a new dish of human feeders. Prior to electroporation, hES3 cells were split by trypsin digestion for 4 to 6 passages. About 30 million cells were harvested and mixed with 40 ug of linearized MHCneo (FIG. 13 A; previously described by Klug et al, JCI 1996) plasmid DNA in 0.8 ml of media. Cells were electroporated with a Bio-Rad GenePulser XL set to 320V and 200 µF. Transfected cells were plated on hygromycin-resistant mouse embryonic fibroblasts (Specialty Media, USA) at a density of 0.4 million cells per square centimeter. One week after plating, 50 µg/ml hygromycin was added to the cells. Colonies that emerged after several weeks were manually picked and expanded.

(ii) Southern Blot Analysis

Genomic DNA was extracted from hES3 clones using the Qiagen DNeasy columns. About 15 µg of DNA was digested with EcoR I and separated on a 1% agarose gel. DNA was transferred to Hybond N+ membrane (Amersham) and blotted with a dioxigenin (DIG) labelled probe against the mouse αMHC promoter sequence. The probe was visualized with anti-DIG antibody conjugated to alkaline phosphatase (Roche Applied Science) and chemiluminescent substrate CDP*Star (New England Biolabs).

II. Results

Hygromycin resistant hES3 colonies emerged several weeks after transfection. Colonies were expanded and screened by southern blot analysis of extracted genomic DNA using a probe for the mouse α-MHC promoter. The generation of a transgenic hES cell line that allows antibiotic selection of cardiomyocytes has been described previously (Loren J Field U.S. Pat. No. 5,733,727 issued 31 Mar. 1998).

Figure 13:
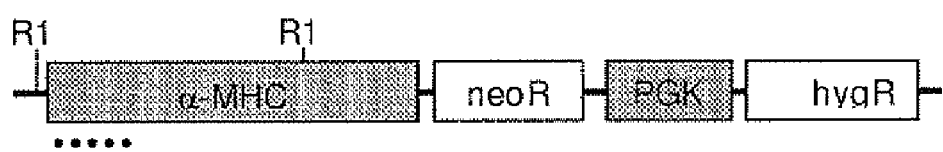
FIG. 13 shows the generation of a transgenic hES cell line that allows antibiotic selection of cardiomyocytes.
Figure 13:
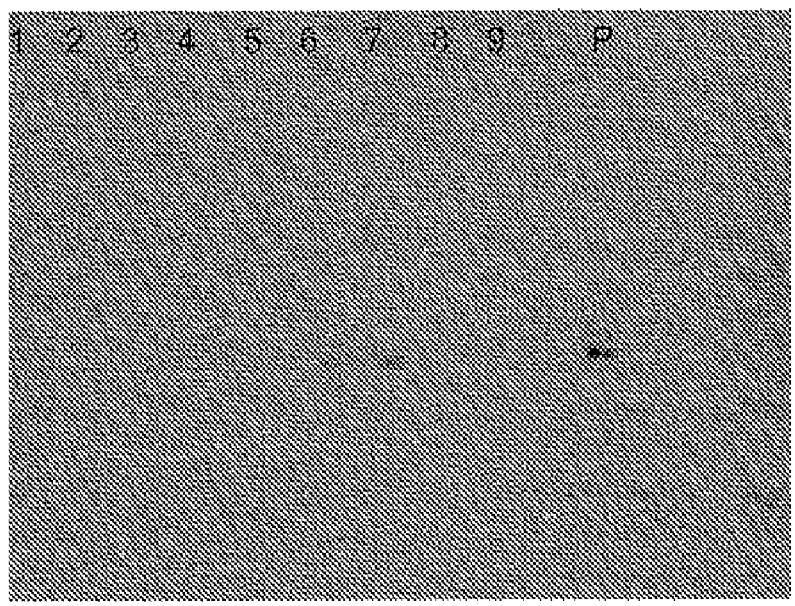

A schematic of the mouse αMHCneo transgenic construct is shown in FIG. 13. R1 denotes EcoR I sites and the dotted line indicates the probe fragment that was used for Southern blot analysis. A Southern blot analysis showed positive bands detected by a probe against mouse α-MHC promoter. Lanes 1-9 are genomic DNA from hygromycin resistant clones and positive clones are shown in lanes 1, 2, 4, 6, and 7. P=α-MHCneo plasmid (FIG. 13B) Southern blot detected the α-MHC neo transgene in the genome of several clones and about half of the clones screened contained the full transgene (FIG. 13B).

III. Summary

Several transgenic hESC cell line were able to be made that contained the selectable αMHC-neo construct described by U.S. Pat. No. 5,733,727. One of these transgenic hES cell lines is used in example 9.

Example 9

Enrichment of Transgenic hES-Derived Cardiomyocytes

I. Materials and Methods

Transgenic hES cells carrying α-MHCneo were differentiated in END-2 conditioned media as described in Example 8 and then selected with 200 g/ml or 400 µg/ml G418 for various periods. Cells were dissociated by trypsin and plated onto chamber slides. Transgenic cardiomyocytes that were not selected with G418 were also plated as a control. Cells were then fixed by 2% paraformaldehyde and stained with the MF-20 antibody, which recognizes cardiac α-MHC. Cells were counterstained with haematoxylin to reveal nuclei. Cells negative for MF-20 staining in each slide preparation were counted and calculated as a percentage of total nuclei.

II. Results

Selection of transgenic cardiomyocytes with G418 resulted in most of the cells being positively stained for cardiac α-MHC. As shown in the Table 3, selection of the transgenic cardiomyocytes with two different G418 concentrations for various days resulted in greater than 99% of the cells positive for the cardiac marker. These results illustrate the effectiveness of lineage selection to enrich for human cardiomyocytes.

TABLE 3

| | Total nuclei | α-MHC negative | Percent cardiomyocytes |
|---|---|---|---|
| No selection | 3018 | 2646 | 12.33% |
| G418-selection at 200 µg/ml for 10 days | 1021 | 10 | 99.02% |
| G418-selection 200 µg/ml for 16 days | 2238 | 18 | 99.20% |
| G418-selection 400 µg/ml for 7 days | 2046 | 3 | 99.85% |
| G418-selection 400 µg/ml 13 days | 1058 | 5 | 99.53% |

III. Summary

Using the antibiotic G418 cardiomyocyte populations could be effectively used over period of several days in culture to generate populations of cell that contained cardiomyocytes that were substantially enriched.

Example 10

Characterization of Selected Cardiomyocytes by Microelectrode Array

I. Materials and Methods

H3M11, one of the transgenic hES lines carrying the mouse α-MHCneo transgene, was differentiated in END-2 conditioned media to induce cardiomyocytes and then selected with G418 for 1 week. G418-selected H3M11 cardiomyocytes were dissociated and plated on microelectrode array chips each containing 64 electrodes (Multi Channel Systems MCS GmbH, Reutlingen, Germany). Extracellular recordings were made with the MEA1060 amplifier and MC-Rack software. Sampling rate was 10 kHz. A control recording was made before addition of compounds. Isoproterenol and E-4031 (Sigma Aldrich) were dissolved in water and added to the MEA chamber and allowed to equilibrate for 10-30 min.

II. Results

Figure 14:
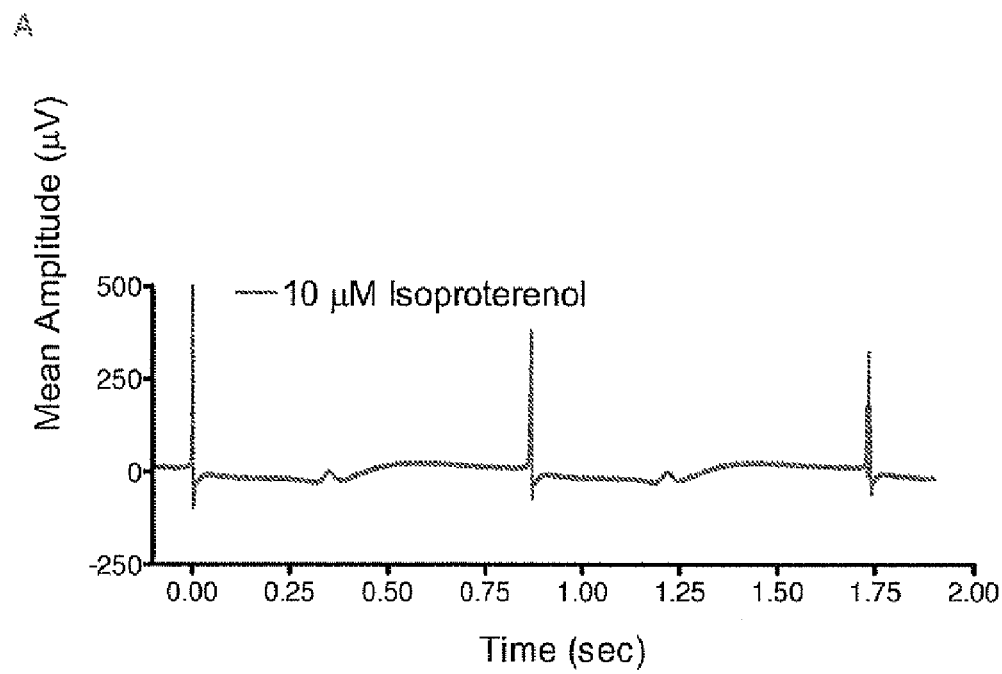
FIG. 14 shows field potentials generated by H3M11 cardiomyocytes as measured by a microelectrode array.
Figure 14:
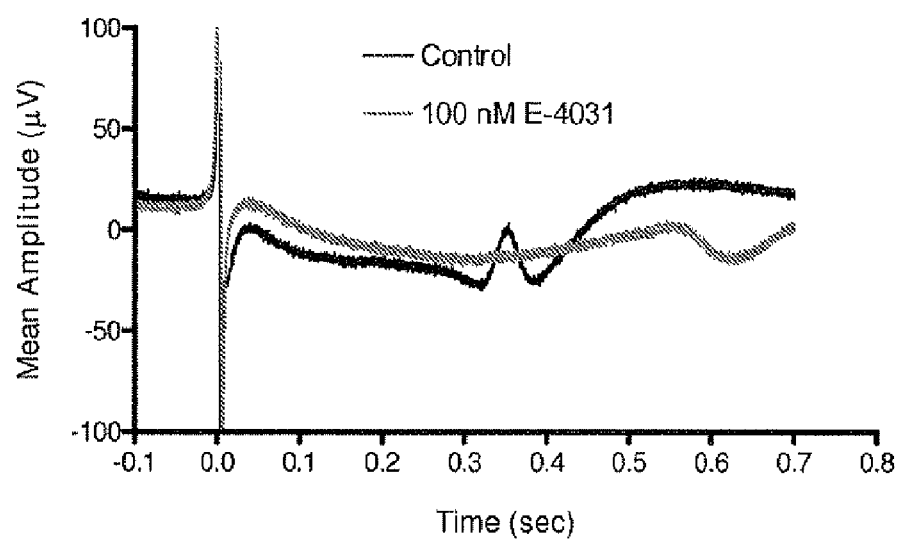

H3M11 cardiomyocytes showed spontaneous cardiac action potential similar to ventricular cardiomyocytes (FIG. 14). Addition of 10 µM isoproterenol, a β-adrenergic agonist, increased beating frequency from 46 beats/min to 70 beats/min (FIG. 14A). Addition of 100 nM E-4031, a blocker of the hERG potassium channel, increased the QT interval from 350 ms to 580 ms (FIG. 14 B). These results show that the H3M11 cardiomyocytes exhibit electrophysiological and pharmacological properties of human cardiomyocytes and could be useful in an assay to predict QT prolongation for drug safety.

III. Summary

These results have demonstrated that highly enriched functional human cardiomyocytes are able to be that are responsive to known pharmacological compounds that can affect cardiomyocyte activity.

REFERENCES

1. Brand, T, Heart development: molecular insights into cardiac specification and early morphogenesis (review) Developmental Biology (2003) 258: 1-19
2. Mummery, C. L., van Achterberg, T. A., van den Eijnden-van Raaij, A. J., van Haaster, L., Willemse, A., de Laat, S. W., and Piersma, A. H. (1991) *Differentiation* 46, 51-60
3. Mummery, C., Ward-van Oostwaard, D., Doevendans, P., Spijker, R., van den Brink, S., Hassink, R., van der Heyden, M., Opthof, T., Pera, M., de la Riviere, A. B., Passier, R., and Tertoolen, L. (2003) *Circulation* 107, 2733-2740
4. van den Eijnden-van Raaij, et al, Differentiation of aggregated murine p19 embryonal carcinoma cells is induced by visceral endoderm-specific FGF-like factor and inhibited by actvin A. Mechanishs of Development (1991) 33:157-166
5. Reubinoff, B. E., Pera, M. F., Fong, C. Y., Trounson, A., and Bongso, A. (2000) *Nat Biotechnol* 18, 399-404
6. Costa, M., Dottori, M., Ng, E., Hawes, S. M., Sourris, K., Jamshidi, P., Pera, M. F., Elefanty, A. G., and Stanley, E. G. (2005) *Nat Methods* 2, 259-260
7. Passier, R., Oostwaard, D. W., Snapper, J., Kloots, J., Hassink, R. J., Kuijk, E., Roelen, B., de la Riviere, A. B., and Mummery, C. (2005) *Stem Cells* 23, 772-780
8. Yong I. Cha, Lilianna Solnica-Krezel b, Raymond N. DuBois, Fishing for prostanoids: Deciphering the developmental functions of cyclooxygenase-derived prostaglandins, Developmental Biology, doi:10.1016/j.ydbio.2005.10.013
9. Lim, H, and Dey, SK Minireview: A Novel Pathway of Prostacyclin Signaling—Hanging Out with Nuclear Receptors, Endocrinology (2005) 143(9):3207-3210
10. Michael Lehrke and Mitchell A. Lazar, The Many Faces of PPARγ, Cell (2005), 123 page 993-999
11. Whittle B J, Moncada S, Whiting F, Vane J R Carbacyclin—a potent stable prostacyclin analogue for the inhibition of platelet aggregation. Prostaglandins (1980) 19:605-627
12. Town M H, Schillinger E, Speckenbach A, Prior G Identification and characterisation of a prostacyclin-like receptor in bovine coronary arteries using a specific and stable prostacyclin analogue, ciloprost, as radioactive ligand. Prostaglandins (1982) 24:61-72
13. Sturzebecher S, Haberey M, Muller B, Schillinger E, Schroder G, Skuballa W, Stock G, Vorbruggen H, Witt W, Pharmacological profile of a novel carbacyclin derivative with high metabolic stability and oral activity in the rat. Prostaglandins (1986) 31:95-109
14. Klug M G, Soonpaa M H, Koh G Y, Field L J. Genetically selected cardiomyocytes from differentiating embronic stem cells form stable intracardiac grafts. J Clin Invest. 1996 Jul. 1; 98(1):216-24

Finally, the invention as hereinbefore described is susceptible to variations, modifications and/or additions other than those specifically described and it is understood that the invention includes all such variations, modifications and/or additions which may be made it is to be understood that various other modifications and/or additions which fall within the scope of the description as hereinbefore described.

The invention claimed is:

1. A method of inducing or enhancing cardiomyocyte differentiation of a stem cell, the method comprising culturing the stem cell in the presence of prostacyclin (PGI2), or an analogue or functional equivalent thereof, alone or in combination with an essential mineral, a small molecule or a protein growth factor of the FGF, IGF, or BMP family thereby inducing or enhancing cardiomyocyte differentiation of a stem cell.

2. A method of inducing or enhancing cardiomyocyte differentiation of a pluripotent stem cell, the method comprising culturing the stem cell in the presence of a gene product expressed by a gene listed in Table 1.

3. A method of inducing or enhancing cardiomyocyte differentiation in a stem cell said method comprising culturing the stem cell in a culture medium in which the effect caused by insulin, or an analogue thereof, is reduced.

4. A method according to claim 1 wherein the protein growth factor of the FGF, IGF or BMP family is selected from the group comprising FGF-2, IGF-1, BMP2, BMP4, BMP6 and homologues and functional equivalents thereof.

5. A method according to claim 1, wherein the small molecule is a p38 MAPK inhibitor.

6. A method according to claim 5, wherein the p38 MAPK inhibitor is SB203580.

7. A method according to claim 1, 2 or 3, further comprising culturing the stem cell in the presence of transferrin or selenium.

8. A method according to claim 1, 2 or 3, further comprising co-culturing the stem cell with an embryonic cell.

9. A method according to claim 8, wherein the embryonic cell is a visceral endoderm or visceral endoderm-like cell.

10. A method according to claim 8, wherein the embryonic cell is an END2 cell.

11. A method according to claim 1, 2 or 3, further comprising co-culturing the stem cell with an embryonic cell and wherein the embryonic cell expresses a gene product expressed by a gene listed in Table 1.

12. A method according to claim 1 or 2, further comprising culturing the stem cell in a culture medium in which the effect caused by insulin, or an analogue thereof, is reduced.

13. A method according to claim 12, wherein the effect caused by insulin, or an analogue thereof, is reduced by culturing the stem cell in the absence of insulin, or an analogue thereof, or by depleting insulin, or an analogue thereof, from the culture medium.

14. A method according to claim 1, further comprising culturing the stem cell in the presence of a gene product expressed by a gene listed in Table 1.

* * * * *